(12) United States Patent
Friedlander et al.

(10) Patent No.: US 11,096,594 B2
(45) Date of Patent: *Aug. 24, 2021

(54) MULTI-USE ENDOSCOPE WITH INTEGRATED DEVICE-PATIENT MONITORING AND PATIENT-PROVIDER POSITIONING AND DISASSOCIATION SYSTEM

(71) Applicant: The Regents of the University of Colorado, a Body Corporate, Denver, CO (US)

(72) Inventors: Joel Friedlander, Englewood, CO (US); Jeremy Prager, Englewood, CO (US); Emily Deboer, Denver, CO (US); Robin Deterding, Boulder, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/218,614

(22) Filed: Mar. 31, 2021

(65) Prior Publication Data

US 2021/0212577 A1 Jul. 15, 2021

Related U.S. Application Data

(63) Continuation of application No. 16/573,567, filed on Sep. 17, 2019, which is a continuation-in-part of
(Continued)

(51) Int. Cl.
*A61B 90/00* (2016.01)
*A61B 1/233* (2006.01)
(Continued)

(52) U.S. Cl.
CPC .......... *A61B 5/02055* (2013.01); *A61B 1/233* (2013.01); *A61B 3/111* (2013.01);
(Continued)

(58) Field of Classification Search
CPC .......... A61B 1/233; A61B 1/00002–32; A61B 2090/3945
See application file for complete search history.

(56) References Cited

U.S. PATENT DOCUMENTS

| | | |
|---|---|---|
| 3,913,568 A | 10/1975 | Carpenter |
| 4,919,112 A | 4/1990 | Siegmund |

(Continued)

FOREIGN PATENT DOCUMENTS

| | | |
|---|---|---|
| JP | S50-075794 | 11/1948 |
| JP | S60-182928 A | 9/1985 |

(Continued)

OTHER PUBLICATIONS

Nasal endoscopy, https://www.gosh.nhs.uk/teenagers/tests-and-treatments/nasal-endoscopy/ (Year: 2013).*

(Continued)

*Primary Examiner* — Thaddeus B Cox
(74) *Attorney, Agent, or Firm* — Amin Talati Wasserman LLP; J. Peter Paredes

(57) ABSTRACT

A system having a scope with a longitudinal length extending between a proximal end and a distal end includes a plurality of markers spaced along the longitudinal length. The system also includes a disassociation and positioning device that is configured to enhance unsedated transnasal endoscopic procedures by at least partially occluding the vision of a patient while enabling body cavity access, and optionally record and sense body functions such as temperature, heart rate and oxygenation of the blood stream. The system further includes a sensor integrated into the distrac- (Continued)

tion device, wherein the sensor is configured to detect the markers on the longitudinal length of the scope.

15 Claims, 32 Drawing Sheets

Related U.S. Application Data application No. 15/853,521, filed on Dec. 22, 2017, which is a continuation-in-part of application No. 15/850,939, filed on Dec. 21, 2017, now abandoned, and a continuation-in-part of application No. PCT/US2016/039352, filed on Jun. 24, 2016.

(60) Provisional application No. 62/184,077, filed on Jun. 24, 2015, provisional application No. 62/732,272, filed on Sep. 17, 2018.

(51) Int. Cl.

| | |
|---|---|
| *A61B 5/0205* | (2006.01) |
| *A61B 5/06* | (2006.01) |
| *A61B 5/01* | (2006.01) |
| *A61B 3/16* | (2006.01) |
| *A61B 3/11* | (2006.01) |
| *A61B 5/12* | (2006.01) |
| *A61B 5/03* | (2006.01) |
| *A61B 7/00* | (2006.01) |
| *A61B 5/00* | (2006.01) |
| *A61B 5/1455* | (2006.01) |
| *A61B 5/145* | (2006.01) |
| *G06F 3/14* | (2006.01) |
| *A61B 5/08* | (2006.01) |
| *A61B 5/021* | (2006.01) |
| *A61B 5/024* | (2006.01) |

(52) U.S. Cl.
CPC .............. *A61B 3/112* (2013.01); *A61B 3/16* (2013.01); *A61B 5/01* (2013.01); *A61B 5/03* (2013.01); *A61B 5/062* (2013.01); *A61B 5/126* (2013.01); *A61B 5/14517* (2013.01); *A61B 5/14552* (2013.01); *A61B 5/442* (2013.01); *A61B 7/003* (2013.01); *A61B 90/39* (2016.02); *G06F 3/14* (2013.01); *A61B 5/021* (2013.01); *A61B 5/024* (2013.01); *A61B 5/082* (2013.01); *A61B 5/0816* (2013.01); *A61B 2090/3945* (2016.02); *A61B 2090/3954* (2016.02)

(56) References Cited

U.S. PATENT DOCUMENTS

| | | | |
|---|---|---|---|
| 5,125,395 | A | 6/1992 | Adair |
| 5,474,063 | A | 12/1995 | Riendeau |
| 5,624,379 | A | 4/1997 | Ganz et al. |
| 6,017,340 | A | 1/2000 | Cassidy et al. |
| 6,030,360 | A | 2/2000 | Biggs |
| 6,241,657 | B1 | 6/2001 | Chen et al. |
| 6,458,076 | B1 | 10/2002 | Pruitt |
| 6,585,639 | B1 | 7/2003 | Kotmel et al. |
| 6,994,667 | B2 | 2/2006 | Singh |
| 8,702,594 | B2 | 4/2014 | Edidin et al. |
| 9,107,573 | B2 | 8/2015 | Birnkrant |
| 9,848,761 | B2 | 12/2017 | Demers et al. |
| 2004/0176683 | A1 | 9/2004 | Whitin et al. |
| 2004/0220451 | A1 | 11/2004 | Gravenstein et al. |
| 2005/0197536 | A1 | 9/2005 | Banik |
| 2005/0235422 | A1 | 10/2005 | Wallace |
| 2007/0167967 | A1 | 7/2007 | Mikkaichi et al. |
| 2007/0203393 | A1 | 8/2007 | Stefanchik |
| 2008/0154090 | A1 | 6/2008 | Hashimshony |
| 2008/0262468 | A1 | 10/2008 | Clifford et al. |
| 2009/0318798 | A1 | 12/2009 | Singh et al. |
| 2010/0137688 | A1 | 6/2010 | Couvillon, Jr. |
| 2011/0146676 | A1 | 6/2011 | Dallam et al. |
| 2013/0023770 | A1 | 1/2013 | Courtney et al. |
| 2013/0158451 | A1 | 6/2013 | Juto et al. |
| 2013/0172677 | A1 | 7/2013 | Kennedy, II et al. |
| 2013/0249787 | A1 | 9/2013 | Morimoto |
| 2013/0296649 | A1 | 11/2013 | Kirma et al. |
| 2014/0296633 | A1 | 10/2014 | Gumbs et al. |
| 2014/0320617 | A1 | 10/2014 | Parks et al. |
| 2015/0209005 | A1 | 7/2015 | Bezanson et al. |
| 2015/0253574 | A1 | 9/2015 | Thurber |
| 2015/0306340 | A1 | 10/2015 | Giap et al. |
| 2016/0135672 | A1 | 5/2016 | Spinnler et al. |
| 2018/0055347 | A1 | 3/2018 | Teixeira Dos Santos Paulo |
| 2018/0146839 | A1 | 5/2018 | Friedlander et al. |

FOREIGN PATENT DOCUMENTS

| | | |
|---|---|---|
| JP | H03-178631 A | 8/1991 |
| JP | H11-032982 A | 2/1999 |
| JP | 2001-091892 A | 4/2001 |
| JP | 2003-038421 A | 2/2003 |
| JP | 2005-507273 A | 3/2005 |
| JP | 2007-512099 A | 5/2007 |
| JP | 2009-165632 A | 7/2009 |
| JP | 2013-507189 A | 3/2013 |
| WO | 2013-101912 A1 | 7/2013 |
| WO | 2016-210322 A1 | 12/2016 |

OTHER PUBLICATIONS

Chheda, N et al.; "Transnasal Esophagoscopy"; Apr. 21, 2015; Clinical Gate, Chapter 73; https:// clinicalgate.com/transnasal-esophagoscopy/ (Year: 2015).

International Search Report and Written Opinion issued in corresponding foreign application No. PCT/US2016/039352, 8 pages (dated Sep. 14, 2016).

International Search Report and Written Opinion issued in corresponding foreign application No. PCT/US2018/067152, 16 pages (dated Apr. 9, 2019).

International Search Report and Written Opinion issued in corresponding foreign application, PCT/US2019/034954, 9 pages (dated Aug. 8, 2019).

International Search Report and Written Opinion issued in corresponding foreign application, PCT/US2019/051523, 13 pages (dated Jan. 29, 2020).

Office Action issued in corresponding foreign application, JP2017-566710, pp. 1-3 (dated Aug. 11, 2020).

Office Action issued in corresponding foreign application, JP2017-566710, pp. 1-3 (dated Mar. 15, 2021).

\* cited by examiner

SECTION A-A

MULTI-USE ENDOSCOPE WITH INTEGRATED DEVICE-PATIENT MONITORING AND PATIENT-PROVIDER POSITIONING AND DISASSOCIATION SYSTEM

CROSS-REFERENCE TO RELATED APPLICATIONS

This application claims priority to U.S. patent application Ser. No. 16/573,567, filed Sep. 17, 2019, which claims priority to U.S. Provisional Application No. 62/732,272, filed Sep. 17, 2018. U.S. patent application Ser. No. 16/573,567 is also a continuation-in-part application of U.S. application Ser. No. 15/853,521, filed Dec. 22, 2017, which is abandoned and claims benefit to and is a continuation-in-part of International Patent Application Serial No. PCT/US16/39352, filed Jun. 24, 2016, which published as PCT Publication No. WO 2016/210322 on Dec. 29, 2016, which claims benefit of U.S. Provisional Application No. 62/184,077, filed on Jun. 24, 2015. U.S. application Ser. No. 15/853,521 is also a continuation-in-part of U.S. application Ser. No. 15/850,939, filed Dec. 21, 2017.

The foregoing applications, and all documents cited therein or during their prosecution ("appl'n cited documents"), and all documents cited or referenced in the appl'n cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This invention relates to a device and its uses for evaluating multiple conditions. A device as described herein may be capable of being used for multiple end uses, including, for example, an endoscope, such as a nasal endoscope, a transnasal esophagoscope, a transnasal gastroscope, a transnasal duodenoscope, a transnasal enteroscope, a triple endoscope, a bronchoscope, a laryngoscope, a transnasal gastroscope, an aerodigestive scope, and/or an endoscopic device used to visualize any body cavity to which it would fit.

As described herein devices may encompass multiple functionalities while maintaining specific sizes and patient positions to allow for ease of use and/or patient comfort. In some instances, for example, in veterinary medicine and/or medicine, such as in pediatrics or small adults, it may be necessary to create devices having smaller diameters while maintaining the functionality. To create such a small device with full capabilities and keep an unsedated patient in position while interacting with a provider is complicated and technically challenging to accomplish. For example, the evaluation and treatment of eosinophilic esophagitis, esophagitis, Barrett's esophagus, esophageal cancer, gastritis, celiac disease, gastric infection, gastric ulcer, duodenal ulcer and aerodigestive conditions, in children, small adults, and in outpatient or emergent settings where a gastrointestinal procedural suite or operating room are not available may be of particular interest. More specifically, some embodiments of this invention may relate to pediatric or adult nasal endoscopes and patient and provider distraction and interaction devices.

BACKGROUND

Eosinophilic esophagitis (EoE) is an increasingly common chronic inflammatory disease that affects children and adults with an estimated incidence of 1/10,000 in the United States. [Dellon E S, Gonsalves N, Hirano I, et al. ACG clinical guideline: Evidenced based approach to the diagnosis and management of esophageal eosinophilia and eosinophilic esophagitis (EoE). Am J Gastroenterol 2013; 108: 679-92; quiz 693.] Because of its potential to progress to esophageal stricture and the fact that symptoms do not always correlate with degree of eosinophilia, much attention has been paid to repeated assessment of the esophageal mucosa to insure mucosal healing following treatment. In contrast, the risks, cost and time commitment associated with traditional sedated esophagogastroduodenoscopy (EGD) can be significant and have raised concerns for providers and parents alike. [Gleich S J, Flick R, Hu D, et al. Neurodevelopment of children exposed to anesthesia: Design of the Mayo Anesthesia Safety in Kids (MASK) study. Contemp Clin Trials 2014; 41C:45-54.] These dilemmas challenge the gastroenterologist to contemplate if EGD use in EoE is meeting the goal of Berwick's triple aim in healthcare to provide effective treatment, low cost care, and an optimal and safe healthcare experience. [Berwick D M, Nolan T W, Whittington J. The triple aim: care, health, and cost. Health Aff (Millwood) 2008; 27:759-69.] Should EGD with biopsy be performed after each therapeutic change regardless of symptomatology, should EGD be reserved for patients who are not clinically responding to treatment, or should EGD not be performed again if patients are feeling well?

To address these questions, alternative methods are urgently needed to measure esophageal inflammation. While esophagoscopy with biopsies remains the gold standard technique for assessing mucosal inflammation, other technologies such as the Cytosponge, esophageal string test and confocal tethered endomicroscopy have emerged as potential alternatives. [Furuta G T, Kagalwalla A F, Lee J J, et al. The oesophageal string test: a novel, minimally invasive method measures mucosal inflammation in eosinophilic oesophagitis. Gut 2013; 62:1395-405; Tabatabaei N, Kang D, Wu T, et al. Tethered confocal endomicroscopy capsule for diagnosis and monitoring of eosinophilic esophagitis. Biomed Opt Express 2013; 5:197-207; Katzka D A, Geno D M, Ravi A, et al. Accuracy, safety, and tolerability of tissue collection by Cytosponge vs endoscopy for evaluation of eosinophilic esophagitis. Clin Gastroenterol Hepatol 2015; 13:77-83 e2.] To date, these tools, while less invasive, are still available only in research settings. [Dellon E S, Gonsalves N, Hirano I, et al. Am J Gastroenterol 2013; 108: 679-92; quiz 693; Furuta G T, Kagalwalla A F, Lee J J, et al., Gut 2013; 62:1395-405.]

Recent work has led to the development of trans-nasal endoscopy/esophagoscopy (TNE) to assess the esophageal mucosa in adults. [Birkner B, Fritz N, Schatke W, et al. A prospective randomized comparison of unsedated ultrathin versus standard esophagogastroduodenoscopy in routine outpatient gastroenterology practice: does it work better through the nose? Endoscopy 2003; 35:647-51; Dumortier J, Josso C, Roman S, et al. Prospective evaluation of a new ultrathin one-plane bending videoendoscope for trans-nasal EGD: a comparative study on performance and tolerance.

Gastrointest Endosc 2007; 66:13-9; Dumortier J, Ponchon T, Scoazec J Y, et al. Prospective evaluation of trans-nasal esophagogastroduodenoscopy: feasibility and study on performance and tolerance. Gastrointest Endosc 1999; 49:285-91; Hu C T. Gauze pledgetting versus endoscopic-guided aerosolized spray for nasal anesthesia before trans-nasal EGD: a prospective, randomized study. Gastrointest Endosc 2010; 71:11-20; Mokhashi M S, Wildi S M, Glenn T F, et al. A prospective, blinded study of diagnostic esophagoscopy with a superthin, stand-alone, battery-powered esophagoscope. Am J Gastroenterol 2003; 98:2383-9; Mulcahy H E, Riches A, Kiely M, et al. A prospective controlled trial of an ultrathin versus a conventional endoscope in unsedated upper gastrointestinal endoscopy. Endoscopy 2001; 33:311-6; Yagi J, Adachi K, Arima N, et al. A prospective randomized comparative study on the safety and tolerability of trans-nasal esophagogastroduodenoscopy. Endoscopy 2005; 37:1226-31.] In contrast to traditional EGDs, TNE offers advantages, including that it can be performed in an outpatient clinic room, requires no anesthesia or sedation, uses an adult trans-nasal gastroscope that is tolerated by adults and procures samples adequate for assessment of Barrett's Esophagus. [Shariff M K, Bird-Lieberman E L, O'Donovan M, et al. Randomized crossover study comparing efficacy of trans-nasal endoscopy with that of standard endoscopy to detect Barrett's esophagus. Gastrointest Endosc 2012; 75:954-61; Saeian K, Staff D M, Vasilopoulos S, et al. Unsedated trans-nasal endoscopy accurately detects Barrett's metaplasia and dysplasia. Gastrointest Endosc 2002; 56:472-8.] However, the endoscopes used in the adult procedures are not appropriate for use in pediatric setting and too large for many adults. To accomplish TNE, many features have been removed and sacrifices have been made, such as the loss of distal steering and decreased visualization. Further, adult endoscopes and nasal endoscopes have large bulky heads, will not fit in many pediatric size or small adult nasal passages, are hard to control by individuals with small hands, do not have optional stiffening capability for improved maneuverability, do not have foot controls or a full array of hand button controls, are not connected to or allow voice dictation of reports, are not able to be used in pediatrics or small adults, and are unable to be used for bronchoscopy. Accordingly, what is needed is a device and associated methodology that can be used to adapt TNE to assess the esophageal mucosa, gastric, and duodenal, tracheal, and bronchial mucosa in children and small adults in both a sedated and unsedated manner with a full array of steering and a channel large enough to enable diagnostics and therapeutics while also allowing full satisfactory evaluation of the above tissues. The present invention provides tools and techniques to meet this important need. Light may be used in medical devices to aid treatment or diagnose conditions with endoscopic technologies. In particular, light may be used on probes to stimulate tissue. For example, gallium nitride microLEDs have been used on probes to stimulate light sensitive tissue as is disclosed by McAlinden (McAlinden, Niall and Massoubre, David and Richardson, Elliot and Gu, Erdan and Sakata, Shuzo and Dawson, Martin D and Mathieson, Keith (2013) Thermal and optical characterization of micro-LED probes for in vivo optogenetic neural stimulation. Optics Letters, 38 (6). pp. 992-94. http://dx.doi.org/10.1364/OL.38.000992), which is incorporated by reference.

During an endoscopic procedure, patients are often fearful and anxious and experience discomfort, and thus it is desirable to distract patients from stimulating their senses, thereby making the procedure mentally and physically easier on the patient. However, this is not enough as the patient often needs to be disassociated from their provider or the experience. The provider also needs to maintain proper position and interaction with a seated patient. There is fear of looking at the medical device or into their providers eyes from a close distance. Further the provider doing an unsedated procedure often needs to be disassociated from their patient due to fear of performing a procedure without anesthesia or sedation as is usually used in such procedures. This same provider needs to keep the patient still and be able to interact in a limited manner with their patient. Such a task in essence is anesthesia without the use of medication or drug. The present disclosure accomplishes this provider and patient dissociation and proper seated positioning while also enabling an easy insertion of the endoscope in a body cavity. These concepts are especially true when treating children, as children are less likely to stay still and have significant anxiety in a clinical setting and throughout the endoscopic procedure with long and uncomfortable devices inserted inside of them.

Citation or identification of any document in this application is not an admission that such document is available as prior art to the present invention.

SUMMARY OF THE INVENTION

In one aspect of the present disclosure, a system is provided. The system comprises a scope comprising a longitudinal length extending between a proximal end and a distal end, the scope further comprising a plurality of markers spaced along the longitudinal length. The system further comprises a patient-provider disassociation device, wherein the device is configured to at least partially occlude the vision of a patient, thereby providing a disassociating and/or distraction environment to the patient, provide proper seated positioning, and enable easy access to the body cavities to which the endoscope is being inserted. The system further comprises a sensor integrated into the disassociation device, wherein the sensor may be configured to detect the markers on the longitudinal length of the scope. The sensor may also be useful for other sensing events or additional sensors may be used for other sensing events.

In another aspect of the present disclosure, the disassociation device may comprise goggles, wherein the goggles are attachable to the patient's face to at least partially occlude the vision of the patient, wherein the goggles comprise a viewable area or region that may include a display, screen, etc. configured to display information, including but not limited to videos, images, text, emojis, indicia, designs, drawings, etc. for viewing by the patient to provide a dissociative experience. In another aspect, the viewable area or region may include a mobile device that has a display or screen, and the goggles further comprise an attachment mechanism to detachably attach the mobile device to the goggles. In yet another aspect, the viewable area or region may include one or more displays or screens integrated into the goggles. The viewable screen may be positioned via the design of the goggles to enable easy access to the nasal cavity by the provider. This is done via the lens angle and shape of the goggle device. This also enables the nasal access for children and adults. In still another aspect, the goggles may further comprise an electroacoustic transducer or loudspeaker configured as headphones or open to air audio transmission device configured to provide audio stimuli to the patient and examiner. In a further aspect, the sensor may be configured to detect the position of the scope within the patient's body via detection of the markers on the longitudinal length of the scope. In still a further aspect, the sensor may be a magnetic sensor and the markers may comprise a metallic material, wherein the magnetic sensor is configured to detect the presence of the markers. In another aspect, the sensor may be a light sensor and the markers may emit or reflect light, wherein the light sensor is configured to detect the presence of the markers. In yet another aspect, the sensor may be a mechanical sensor and the markers may be raised with respect to a surface of the longitudinal length of the scope, wherein the mechanical sensor is configured to detect the presence of the markers or pressure transmitted by the body cavity upon the scope at various distances from the tip of the scope. In still a further aspect, the sensor may be integrated into a nose-piece of the goggles. In another aspect, the scope may be a trans-nasal endoscope. In still another aspect, the sensor (or multiple sensors) may be further configured to detect at least one or multiple of the patient's heart rate, pulse oximetry, blood pressure, sweat content, gas exhalation levels, body temperature, exhalation sounds, respiratory rate, skin elasticity, ocular pressure, pupil sizes, pupil distances, tympanic membrane compliance, and hearing aid function. In one aspect, the distraction device may comprise a recess configured to removably receive an electronics module, wherein the electronics module comprises one or more of the sensors described above.

In another aspect of the present disclosure, a system is provided that comprises a scope comprising a longitudinal length extending between a proximal end and a distal end. The system further comprises a distraction and disassociation device attachable to a patient's head, wherein the distraction device is configured to at least partially occlude the vision of the patient and the viewable image to allow easy access to the nares for a medical procedure. The patient may be positioned in a seated position. Further, the distraction device comprises a proximal portion and a distal portion, wherein the proximal portion is aligned with the patient's natural line of sight and the distal portion is disposed at an angle with respect to the proximal portion.

In one aspect, the scope may be a trans-nasal endoscope and the distraction and disassociation device may comprise at least one screen configured to display videos or images for viewing by the patient, wherein the angle of the distal portion permits access to a nasal passageway of the patient when the distraction device is attached to the patient's head. The distraction device may also further comprise a cutout that permits access to the nasal passageway of the patient when the distraction device is attached to the patient's head.

In another aspect of the present disclosure, a method of conducting an endoscopy exam on a patient by a provider in close proximity to a patient is provided. The method comprises placing a distraction and disassociation device over the patient's eyes to at least partially occlude the vision of the patient, wherein the distraction device comprises a proximal portion aligned with the patient's natural line of sight and a distal portion disposed at an angle above the patient's natural line of sight to expose a nasal passageway of the patient. This same device enables easy access to the nasal cavity due to the shape of the device. The method further comprises inserting at least a portion of an endoscope into the nasal passageway of the patient and conducting one or more assessments of the patient using the endoscope.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. .sctn. 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises," "comprised," "comprising" and the like can have the meaning attributed to it in U.S. Patent law; e.g., they can mean "includes," "included," "including," and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
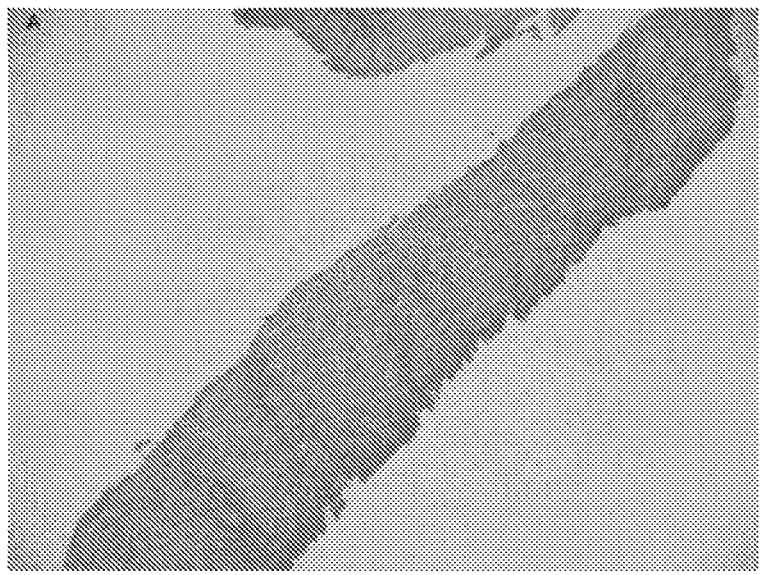
FIG. 1 is an image showing a biopsy with active EoE using a standard 2.8 mm EGD forceps. The surface area is 0.10 mm$^2$.
Figure 2:
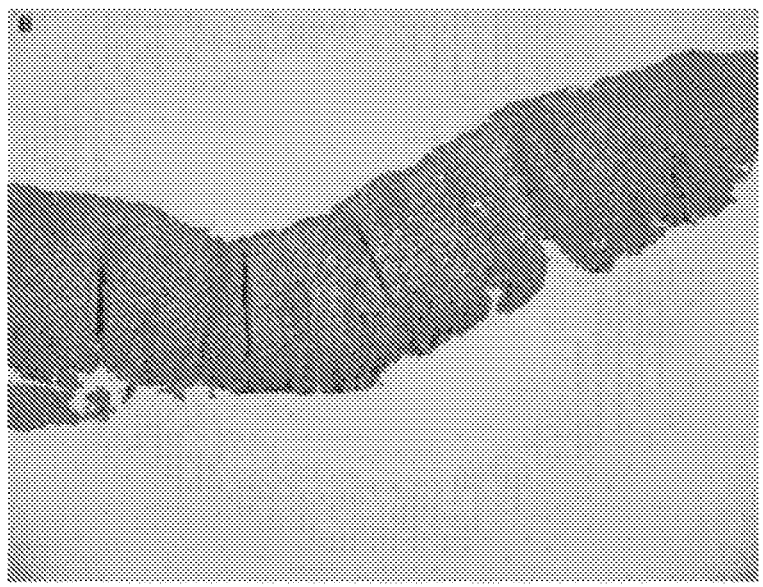
FIG. 2 is an image showing a biopsy from the same patient with active EoE using THE 1.2 mm forceps. The surface area is 0.12 mm$^2$.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The present disclosure documents the performance of TNE with biopsies using these ultra-slim flexible endoscopes to assess the esophageal, gastric, duodenal, tracheal, and bronchial mucosa in pediatric subjects with EoE. The performance was assessed in part through the evaluation of parental and patient subject responses to TNE, the assessment of the ability to procure samples that would be adequate to monitor disease, monitoring adverse events, and recording procedure duration and charges generated. This assessment showed that unsedated trans-nasal endoscopy using the pediatric nasal endoscope and gastroscope and esophagoscope and duodenoscope disclosed herein offers an excellent alternative to sedated esophagogastroduodenoscopy.

Unsedated trans-nasal endoscopy (TNE) in adults is safer and less costly than sedated esophagogastroduodenoscopy (EGD). TNE with biopsies can be adapted as an effective tool to monitor the esophageal, gastric, and duodenal mucosa of children with eosinophilic esophagitis (EoE) or other conditions of the upper gastrointestinal tract with the proper tools and techniques. This technique can dramatically increase the safety and decrease cost in the care of children. The present disclosure documents the development of the performance of TNE with biopsies in pediatric EoE.

Subjects between 8 and 17 years of age with EoE, and their parents, were enrolled in the study. Unsedated TNE was performed. The currently available smaller endoscopes designed for bronchoscopy as a 2.8 mm (1.2 mm channel) or a 4 mm flexible bronchoscope (2 mm channel) were used, and esophageal biopsies were procured. These scopes were shorter than Applicants' currently proposed pediatric nasal endoscope and were without water channels, suction, air, foot control, high definition optics, or stiffening capability. Biopsy analysis, duration, adverse events, and billing charges of TNE were assessed. Immediately after TNE and a minimum of 2 weeks later, the mGHAA-9 (modified Group Health Association of America) and a preference questionnaire were completed, respectively.

Twenty-one of 22 enrolled subjects completed TNE. TNE was tolerated with no significant adverse events. Histopathological analysis revealed 0 eos/hpf (n=12), <15 eos/hpf (n=4), and >15 eos/hpf (n=5) and total epithelial surface area of mucosal biopsies samples from either TNE forceps compared to those obtained with standard endoscopic forceps was not statistically different. All parents and 76.2% of subjects would undergo the TNE again. TNE was preferred over EGD by 85.7% of parents and 52.4% of subjects. mGHAA-9 revealed a high degree of satisfaction (average 43.19+/−2.6 maximum score-45). Charges associated with TNE were 60.1% less than previous EGDs. The results of this study show that unsedated TNE is a preferred, efficacious, and lower cost procedure when monitoring esophageal mucosa of children with EoE.

The emergence of EoE has led to a renewed interest in determining pathogenic mechanisms of esophageal inflammation and sampling of the esophageal mucosa to assess for mucosal healing. Despite the rapid progress in establishing diagnostic criteria, treatments, and novel genes related to pathogenic mechanisms that can significantly impact EoE patients, limited data is available to document the natural history of EoE. This lack of understanding has led to the present clinical practice of multiple, high-cost, and higher-risk sedated assessments of the esophageal mucosa to ascertain whether eosinophilia has resolved following treatment. If eosinophilia resolves, a predicate determination is made that the likelihood for EoE-related complications is diminished. If eosinophilia persists, efforts are made to resolve inflammation regardless of symptomatology, with its subsequent impact on quality of life and costs of care. In this regard, novel devices and sampling methodologies are urgently needed. To address this and offer a new tool in the evaluation of EoE, Applicants sought to determine if TNE could sample the esophageal mucosa in a way that was well-tolerated and adequate. In light of the emergent need for more efficient methods of esophageal mucosal evaluation in EoE, Applicants performed this study within the confines of a multidisciplinary team to perform TNE with biopsies in a pediatric population. Applicants chose this population because of the urgent need to minimize the repetitive risks of anesthesia, improve the understanding of EoE pathogenesis, and to ultimately identify novel therapeutic targets.

Unsedated TNE is an established technique in a number of pediatric and adult subspecialties, but it has not been used by pediatric gastroenterologists. [Birkner B, Fritz N, Schatke W, et al. *Endoscopy* 2003; 35:647-51; Dumortier J, Josso C, Roman S, et al. *Gastrointest Endosc* 2007; 66:13-9; Dumortier J, Ponchon T, Scoazec J Y, et al. *Gastrointest Endosc* 1999; 49:285-91; Hu C T. *Gastrointest Endosc* 2010; 71:11-20; Mokhashi M S, Wildi S M, Glenn T F, et al. Am J Gastroenterol 2003; 98:2383-9; Mulcahy H E, Riches A, Kiely M, et al. *Endoscopy* 2001; 33:311-16; Yagi J, Adachi K, Arima N, et al. *Endoscopy* 2005; 37:1226-31] A number of studies have described the advantages, limitations, and challenges of TNE use, and in 2010, the America Society of Gastrointestinal *Endoscopy* developed a guideline for the use of TNE in adults. [Committee A T, Rodriguez S A, Banerjee S, et al. Ultrathin endoscopes. *Gastrointest Endosc* 2010; 71:893-98; Faulx A L, Catanzaro A, Zyzanski S, et al. Patient tolerance and acceptance of unsedated ultrathin esophagoscopy. *Gastrointest Endosc* 2002; 55:620-23; Faulx A L, Vela S, Das A, et al. The changing landscape of practice patterns regarding unsedated endoscopy and propofol use: a national Web survey. *Gastrointest Endosc* 2005; 62:9-15; Tatsumi Y, Harada A, Matsumoto T, et al. Current status and evaluation of trans-nasal esophagogastroduodenoscopy. *Dig Endosc* 2009; 21:141-46] This guideline increased attention to cost containment, and the recent upswing in interest in esophageal diseases led to renewed interest in this technique. [Faulx A L, Catanzaro A, Zyzanski S, et al. *Gastrointest Endosc* 2002; 55:620-3; Chak A, Alashkar B M, Isenberg G A, et al. Comparative acceptability of trans-nasal esophagoscopy and esophageal capsule esophagoscopy: a randomized, controlled trial in veterans. *Gastrointest Endosc* 2014; 80:774-82; Lin L F, Shen H C. Unsedated trans-nasal percutaneous endoscopic gastrostomy carried out by a single physician. *Dig Endosc* 2013; 25:130-5; Cho S, Arya N, Swan K, et al. Unsedated trans-nasal endoscopy: a Canadian experience in daily practice. *Can J Gastroenterol* 2008; 22:243-6] A recent study also demonstrated the utility of TNE in adults with Barrett's esophagus. [Tatsumi Y, Harada A, Matsumoto T, et al. Current status and evaluation of trans-nasal esophagogastroduodenoscopy. *Dig Endosc* 2009; 21:141-46; Chak A, Alashkar B M, Isenberg G A, et al. Comparative acceptability of trans-nasal esophagoscopy and esophageal capsule esophagoscopy: a randomized, controlled trial in veterans. *Gastrointest Endosc* 2014; 80:774-82; Bush C M, Postma G N. Trans-nasal esophagoscopy. *Otolaryngol Clin North Am* 2013; 46:41-52]. To date, only one study evaluated unsedated transoral endoscopy in children and concluded that it improved time and safety in assessing 21 children for evaluation of abdominal pain, dyspepsia, and dysphagia. [Bishop P R, Nowicki M J, May W L, et al. Unsedated upper endoscopy in children. *Gastrointest Endosc* 2002; 55:624-30]

With the rapidly increasing prevalence of EoE, limited knowledge regarding its pathophysiology, and emerging clinical needs to assess the esophageal mucosa, Applicants sought to determine whether TNE in pediatric EoE would be a feasible and efficacious tool. Results of Applicants' study reveal that patients and their parents experienced with sedated EGD tolerate TNE well, and that patients and their parents prefer TNE compared to EGD. It is likely that the limited side effect profile and complete lack of serious adverse events contributed to the finding that 52.4% of child subjects (4 subjects preferring neither EGD or TNE) and the 85.7% of parents (1 parent preferring neither TNE or EGD) preferred unsedated TNE to sedated EGD. In that parents often make decisions about procedures in pediatrics and a majority of children prefer the procedure, these percentages are indicative of a highly successful alternative to EGD. Immediate benefits of this preference for patients include improved patient satisfaction and increased safety by eliminating anesthesia.

In many ways Applicants' results are quite similar to that reported in adult studies. For example, a large Canadian Study by Cho et al. evaluating 231 patients with an average age of 57 years for routine TNE; their study also found that TNE was well tolerated, safe and feasible. [Cho S, Arya N, Swan K, et al. Unsedated trans-nasal endoscopy: a Canadian experience in daily practice. *Can J Gastroenterol* 2008; 22:243-6] This study was different, however, in that the patients were primarily adults, the scope used was larger (5.3 mm) and duodenal intubation was performed. Applicants' study evaluated the use of 2 smaller endoscopes, smaller biopsy forceps, and TNE performance in children. Some areas of divergence between Applicants' findings and similar adult studies include that (1) in Applicants' study both the parents and child subjects evaluated the technique, (2) the adequacy of smaller forceps to evaluate the esophageal mucosa in EoE was assessed, and (3) the actual rather than contemplative type of future endoscopy preferred by subjects who have undergone multiple previous EGD's was examined. These findings augment the results of this research and its potential application to adult and pediatric endoscopy practices.

Applicants are particularly encouraged by their findings for several reasons. First, there was great interest in this procedure amongst patients and parents. Applicants only needed to screen 22 subjects to enroll the 21 subjects reported here. This is likely explained by the fact that the EoE patient population represents a very engaged, experienced, and educated population that is readily seeking alternative methods. Applicants are highly confident that this is a technically feasible procedure, and are further encouraged by its overall rapid success that was facilitated by a multidisciplinary pediatric team dedicated to the care of children with aerodigestive diseases and EoE. Applicants' study provides strong support for larger studies to validate this approach that will provide novel insights into the natural history of EoE and significantly improve the lives of children with EoE in a safer, cost-effective, and efficacious manner.

Second, Applicants' study found a high level of satisfaction and enthusiasm to repeat the TNE. The overwhelming majority of patients and parents were satisfied and preferred unsedated TNE compared to standard EGD. Subject responses in the qualitative survey identified critical elements including the lack of anesthesia, the presence of parents during the procedure, the limited duration of the procedure and rapid recovery. TNE was safe, as evidenced by the fact that no significant adverse events or event needed subsequent treatment or evaluation. The subjects and parents appreciated the improvement in their quality of life with TNE, as it allowed them the ability to return to school and work and eat shortly afterwards. In fact, several families noted the patients returned to school or a sport activity after the TNE. The time at CHCO for a standard EGD is 3 hours compared to 60-90 minutes for the TNE, a time that included not only the TNE but also research protocol documentation. This 3-hour procedure center time for EGD usually includes check-in, pre-operative evaluation by nursing, gastroenterology, and anesthesia, the procedure itself, recovery, and discharge instructions. The 60-90 minute time for TNE in clinic included research documentation, pre-procedural documentation, the procedure itself, and discharge instructions. Most of these improvements in time reduction and increased satisfaction, noted above, are related to the effects of eliminating anesthesia or sedation for TNE. Not only does this practice seem to improve satisfaction of patients and parents, but there is also a significant likelihood it decreases the risk of adverse medication reactions, aspiration, and possible effects on the developing pediatric brain. [Gleich S J, Flick R, Hu D, et al. Contemp Clin Trials 2014; 41C:45-54] This is an emerging concern amongst pediatric anesthesiologists. While pediatric subjects without sedation or general anesthesia noted a mild sore throat and gagging, this was minor enough that the majority chose follow-up TNE for their EoE evaluation after their initial study procedure. This has been confirmed as more than a hypothetical question, with several of Applicants' subjects requesting follow-up TNE after the study concluded.

The third positive outcome of Applicants' study relates to the integrity of the mucosal sample. Regarding the technique's effectiveness in evaluating mucosal esophageal samples, Applicants found that the epithelial surface area needed for eosinophil count evaluation was not significantly different from the standard EGD 2.8 mm biopsy forceps compared to either of the TNE 2 mm or 1.2 mm biopsy forceps. This finding provides a high level of confidence that the sample procured at the time of TNE will have the same surface area compared to that obtained with the gold standard EGD biopsy forceps. The 2 mm forceps were also able to procure lamina propria.

The final areas of interest in this study were the reduction in cost and increase in efficiency. Financial benefits of TNE include the fact that TNE incurred fewer charges and required less time away from work and school when compared to a standard sedated pediatric EGD. The project demonstrated a significant 60.1% drop in charges. The majority of this reduction in cost is related to the lack of anesthetic/anesthesiologist during TNE. The significance of this cannot be understated. For example, if Applicants' institution were to perform 100 sedated EGDs per year for EoE at a hypothetical average, non-insurance adjusted charge of $9,390 dollars per general anesthesia-provided endoscopy encounter, this would accumulate $939,000 total charges per year for EoE. This would include all facility charges, physician, pathology and anesthesia fees. If these 100 EGDs for EoE were converted to unsedated TNE, this could translate to a healthcare systems charge savings of $564,000 dollars per year. These are possible charges, however, and not respective insurance rates.

Several areas will be addressed in future evaluations. First, for practical reasons, Applicants needed to use two different sized endoscopes for TNE. Future work will standardize this for patient comfort and biopsy size. Second, although the 1.2 mm forceps were not able to procure lamina propria, the 2 mm forceps in this study were able to obtain lamina propria. While this section of the tissue has been used to grade fibrosis, this metric has not been standardized or become a gold standard for clinical assessments. Applicants' study demonstrates feasibility in pediatrics, but evaluating a much larger cohort is required to achieve a significant power for safety and other metrics. Power analysis based on Applicants' own institution's quality and safety data would necessitate over 10,000 endoscopies to find a single significant adverse event. This could be remedied with the development of further databases, as this technique is increasingly used at Applicants' institution or in a national program evaluating its use in pediatrics. Finally, Applicants undertook this study in a multidisciplinary collaboration with their pediatric pulmonary and otolaryngology colleagues. This was done for study design to maximize patient comfort during TNE development in pediatrics, a strong interest in aerodigestive and eosinophilic disorders by gastroenterologists, otolaryngologists, and pulmonologists alike, and the need for a more pragmatic multidisciplinary approach to diagnosing and managing EoE as it presents in different single specialty clinics. Since the study initiation, the gastroenterologist, otolaryngologist, and pulmonologists have been trained in single physician TNE with biopsies that further improves cost and efficiency, diagnosis, and referral for management of EoE.

In conclusion, the implementation of TNE in pediatric gastroenterology for the evaluation of pediatric EoE is safe, preferred by patients and parents alike, and has the potential to dramatically reduce costs. Thus it appears that TNE would be measured as a highly effective practice in pediatric EoE management per Berwick's description of the triple aim: the pursuit of improved experience of care, the health of populations should be improved, and the cost of per capita healthcare should be decreased. [Berwick D M, Nolan T W, Whittington J. *Health Aff (Millwood)* 2008; 27:759-69.] This suggests that TNE use should be highly considered as an alternative to standard sedated EGD or esophagoscopy for the follow-up evaluation of pediatric EoE. The technique will continue to be refined and improved, offering more opportunities for its use in monitoring response to therapeutics, obtaining follow-up evaluations, and performing research in EoE.

Figure 3:
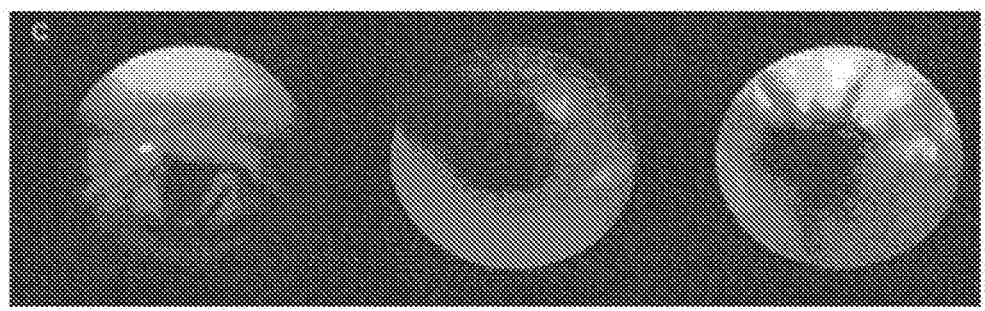
FIG. 3 is an image taken from a subject with active furrowing and eosinophilic exudates.
Figure 4:
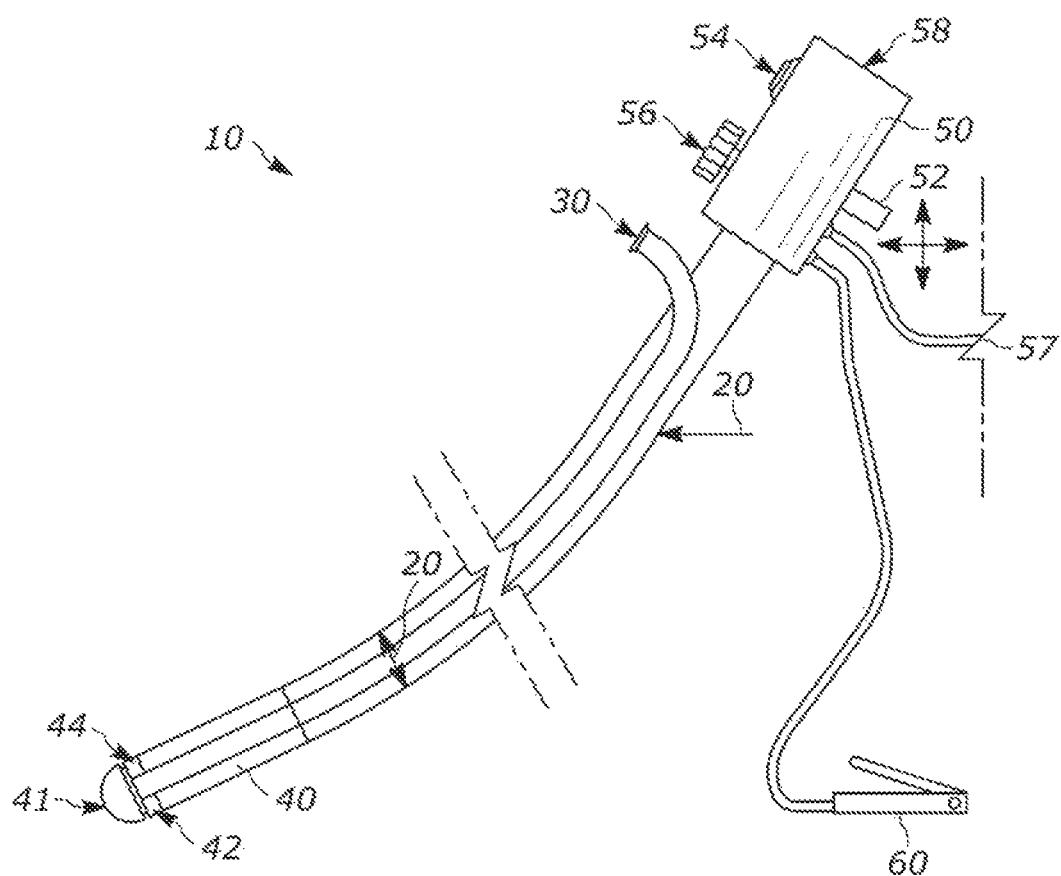
FIG. 4 is a drawing depicting an illustrative example of a pediatric nasal endoscope.

Turning to FIG. 4, a pediatric nasal endoscope 10 was developed to perform TNE in children. The pediatric nasal endoscope 10 includes a flexible endoscope shaft 20 constructed from medical-grade slippery (such as a hydrophobic) material with a slick coating having a length of about 1.05 meters and a width of about 3.5 mm. The flexible endoscope shaft 20, possibly as a single material extrusion, has a biopsy channel 30 running the length of the endoscope shaft and is adapted to slidingly receive a pediatric nasal endoscope biopsy forceps or other medical device 70 (see FIG. 3) within the lumen of the channel or allow suction or irrigation. 30. The distal end 40 of the flexible endoscope shaft 20 is rounded and can be flat or if the end user wishes designed to be terminated with an optional, removable soft silicone tip 41. The distal end 40 of the flexible endoscope shaft 20 also includes a high lumen LED or MicroLED 42 to provide light at the tip and a high-resolution video capture device 44 to capture images or video in the region of the distal end 40 of the flexible endoscope 20. The proximal end 50 of the flexible endoscope shaft 20 can include a single 4-way tip deflection control lever 52 to control the displacement of the endoscope's tip, a button 54 to actuate photo or video and/or autotranscription features associated with reporting system capabilities of the endoscope, a hand control 56 to operate air and/or water suction, a line out 57 to a imaging system such as a computer monitor, an optional scope stiffening device 58 to allow its use in aerodigestive medicine. A foot pedal 60 can also be coupled to the endoscope to activate and control water flow and air suction and/or other control features of the scope.

Figure 5:
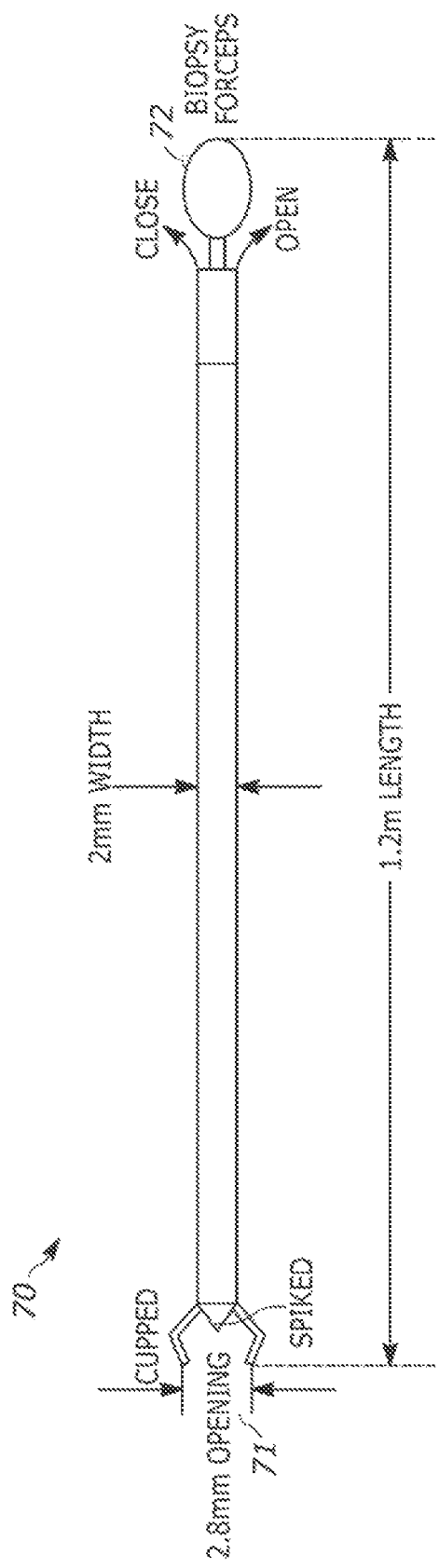
FIG. 5 is a drawing depicting an illustrative example of a pediatric nasal endoscope biopsy forceps.

As discussed above, the flexible endoscope shaft 20 has a biopsy channel 30 running the length of the endoscope and is adapted to slidingly receive a pediatric nasal endoscope biopsy forceps 70 (See FIG. 5) within the lumen of the channel 30. Turning to FIG. 5, an exemplary pediatric nasal endoscope biopsy forceps 70 is illustrated. The pediatric nasal endoscope biopsy forceps 70 has a length of about 1.2 meters, which is slightly longer than the length of the biopsy channel 30, a width of about 1.8-2 mm, and opposing ends forming a distal end 71 and a proximal end 72. The distal end 71 includes a cupped and spiked tip with an opening of about 2.8 mm to 5 mm when fully open. The proximal end 72 includes an actuator to open and close the tip at the distal end 71 of the forceps 70. Examples 1 & 2, presented below, document the development of the trans-nasal endoscopy/esophagoscopy (TNE) to assess the esophageal mucosa in children using the pediatric nasal endoscope.

Further embodiments of endoscopic devices, elements thereof, and/or systems utilizing endoscopes are described herein. Endoscopes may be used in combination with other elements in a system to enhance the capabilities of the scope and/or increase a number of uses for which the scope may be used.

Figure 6:
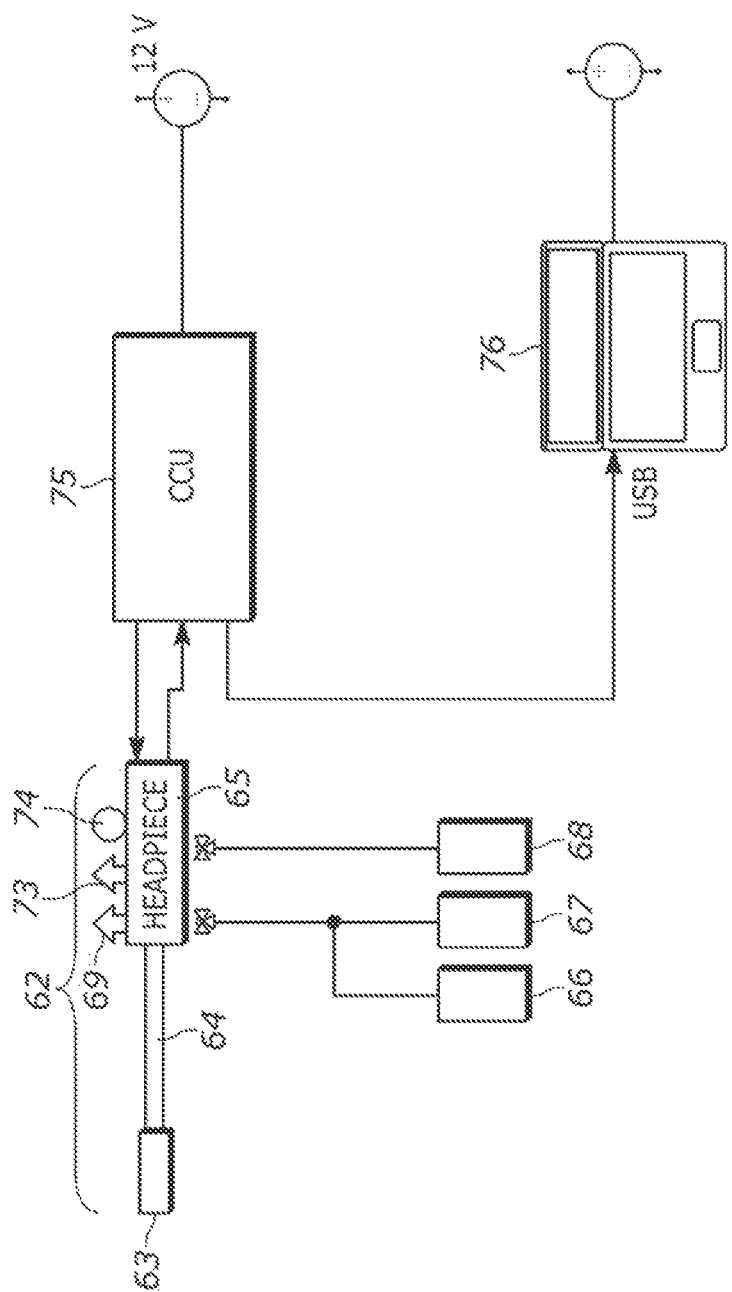
FIG. 6 is a block diagram depicting a system that incorporates an endoscope.

A system including endoscope 62 is shown in FIG. 6. As shown, endoscope 62 includes distal element 63, elongated element 64 and control element 65. An endoscope may be coupled to external supplies and/or reservoirs of materials. As shown in the illustrative example of FIG. 6, endoscope 62 is coupled to air supply 66, liquid supply 67, and suction 68. In addition, endoscope 62 includes interface elements 69, 73. Endoscope 62 is coupled to computer control unit 75 and computer 76.

The control element may include a port or a number of ports which are used to provide and/or remove materials to/from a target area. For example, ports may be used to supply and/or remove fluids to/from a target area, such as water, air, and/or medications in specific measured amounts. In some embodiments, an interface element may be configured to deliver one or more predetermined amounts of water, air and/or medicine during use by the operator based on a procedure, protocol, patient needs (for example, patient size) and/or preferences of the operator. In alternate embodiments, an interface element may be configured to remove predetermined amounts of fluids.

In some instances, suction may connected to a port in order to provide suction to a target area. Ports may include coupling structures to couple various delivery systems to the control element.

Some embodiments of control elements may include interface elements. For example, an interface element may be used to control the positioning and/or functions of the distal element, a portion of the elongated element, the function of devices and/or sensors positioned along the elongated element and/or the distal element. In particular embodiments, an interface element may be used to determine a distance from an insertion point and/or measure luminal body findings. For example, determining a diameter of lumen, such as an esophagus or bronchus, and/or measuring the size a lumen and/or findings therein, such as a gastric polyp or ulcer. For example, interface elements may control aspects of the optical system. In some embodiments, interface elements may control image capture, video, and/or audio recording.

For example, as depicted in FIG. 6, interface element 69 may control the imaging element. In particular, in some instances, an interface element may be programmed such that different user interactions may be recognized by the system as different commands. In particular, interface element 69 may be programmed to capture an image upon a momentary touch. In contrast, interface element 69 may be programmed to start and/or end video capture when the interface element is pressed and held. Further, interface element 73 may be programed such that a touch, for example, a momentary touch, may provide an instruction that the device will auto-populate a section of a report, while a press and hold motion will instruct the device to record audio. For example, the auto-populate feature would enable audio to be transmitted from the microphone in the control element to a reporting system where it would be transcribed into a report system automatically.

In some embodiments, an auto-populate feature may be used to populate any portion of form with transcribed audio data, audio files, video files, metrics measured by sensors, in particular, dimensions, position of the endoscope, and/or other physiological conditions within a body or portion of the body being viewed. In some embodiments the recordings and information by the endoscope could be transmitted to a remote physician for interpretation and consultation.

A control element may include a steering mechanism. For example, FIG. 6 depicts user interface 74 which may be used as a steering mechanism. In some embodiments, the steering mechanism will be a four-way mechanism. For example, the steering mechanism may be constructed along the lines of a joystick and/or roller ball to allow for single hand manipulation and steering.

The control element may have a housing constructed using standard methods known in the art, as well as newly developed technologies. For example, the control element may have a housing that is constructed using three dimensional printing.

Figure 7A:
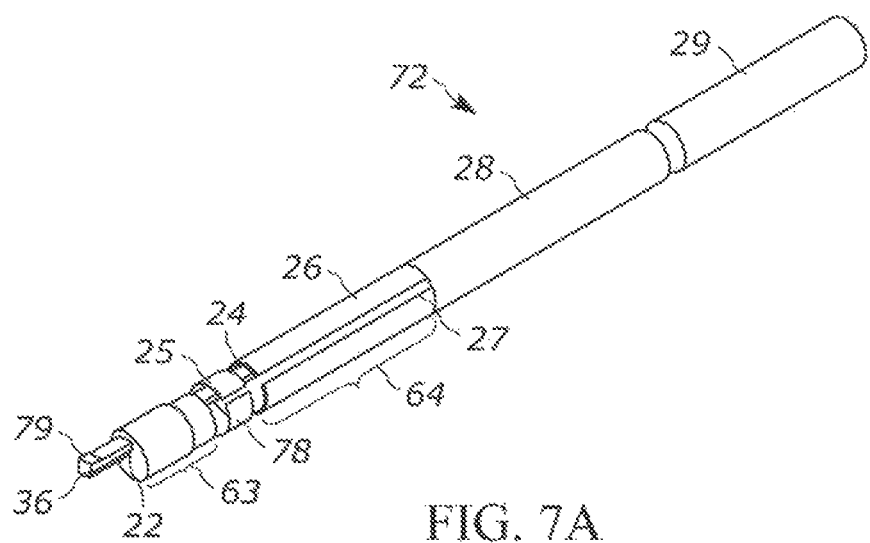
FIG. 7A is an exploded view of an illustrative example of the distal and elongated elements of an endoscope.
Figure 7B:
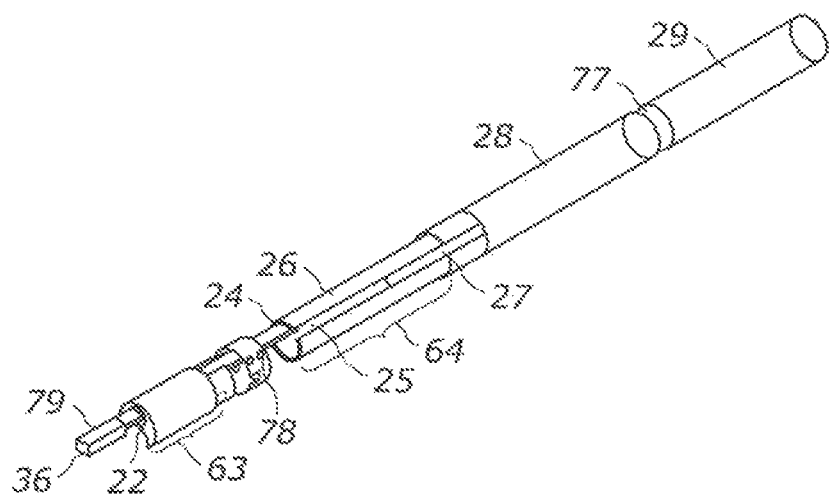
FIG. 7B is an exploded view of an illustrative example of the distal and elongated elements of an endoscope.

FIGS. 7A-B depict exploded partial cutaway views of endoscopes 77. In particular, as shown in FIG. 7A, distal element 63 is positioned proximate to steering collar 78 which is positioned proximate to elongated element 64. As shown, a portion of imaging element 79 extends from the distal element while a portion is positioned in conduit 22 of distal element 63 and extends through steering collar 78 and into conduit 24 of the elongated element 77.

The distal element of the endoscope may have a rounded end, a flat end, and/or a combination. In some embodiments, an end of the distal element may include a soft tip, for example, a soft silicone tip.

Various embodiments of an end view of a distal element are depicted in FIGS. 7A, 7B, 8, 11, 15, 18, 22, 26, 29. Distal elements may be constructed from one or more materials, including but not limited to plastics such as acrylonitrile butadiene styrene (ABS), polycarbonate (PC), polycarbonate-acrylonitrile butadiene styrene (PC/ABS), high density polyethylene (HDPE), polyamide (PA), polyether ether ketone (PEEK), polyether block amide, polypropylene (PP), and/or polyvinyl chloride (PVC), metals such as aluminum, stainless steel, carbon steel, titanium, magnesium, and/or combinations thereof. The material of the endoscope and all enclosed materials may be derived from a single material extrusion without covering. The materials depicted in these various embodiments may be combined based on the needs of the use. An illustrative example of the distal element includes stainless steel.

Elongated elements 77 of FIGS. 7A-B include steering collar 78, extruded element 26, tubular element 28 and shrink element 29. As is shown in FIGS. 7A-B, extruded element is surrounded at least in part by tubular element 28, which is in turn surrounded by the shrink element 29. As can be seen in both FIGS. 7A-B, steering guides 25 are positioned within groove 27 on the extruded element 26. FIG. 7A depicts steering guides connected to the steering collar 78 at groove 27.

Figure 8:
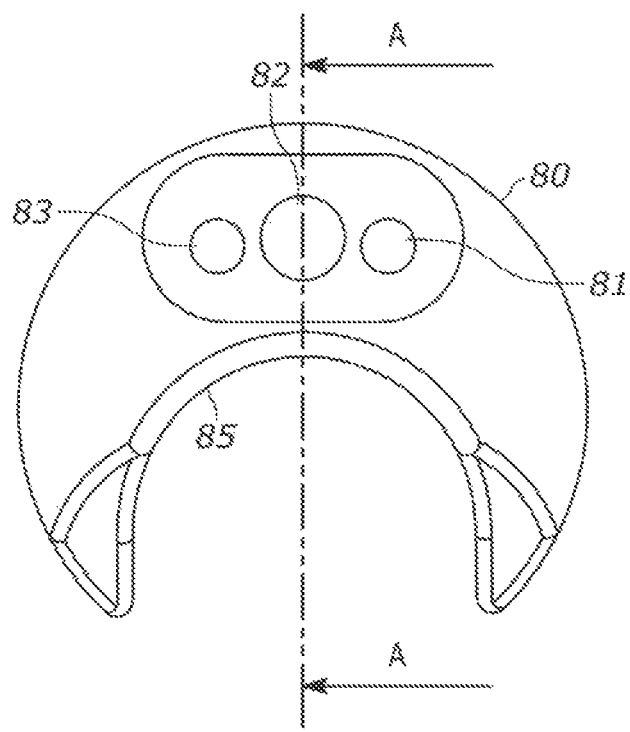
FIG. 8 is a drawing depicting an end view of an illustrative example of a distal element for an endoscope.

As shown in FIG. 8, an end of distal element 80 shows multiple conduits 82, 83, 84. In an embodiment, conduits 82, 83, 84 may be used to house devices and/or portions thereof that are necessary for the functioning of the endoscope. In particular embodiments, one or more of the conduits may be used to house optical fiber. Depending on the design of the endoscope and positioning of various elements therein, the conduits may extend from the distal end to the proximal end of the elongated element. In alternate embodiments, one or more of the conduits may extend from a middle of the elongated element to an end. For example, if an illumination source is positioned at a point corresponding to a middle of the elongated element, a conduit that houses the optical fiber to provide light to the distal element may run from the distal element to the position of the illumination source located at the middle of the elongated element.

Figure 9:
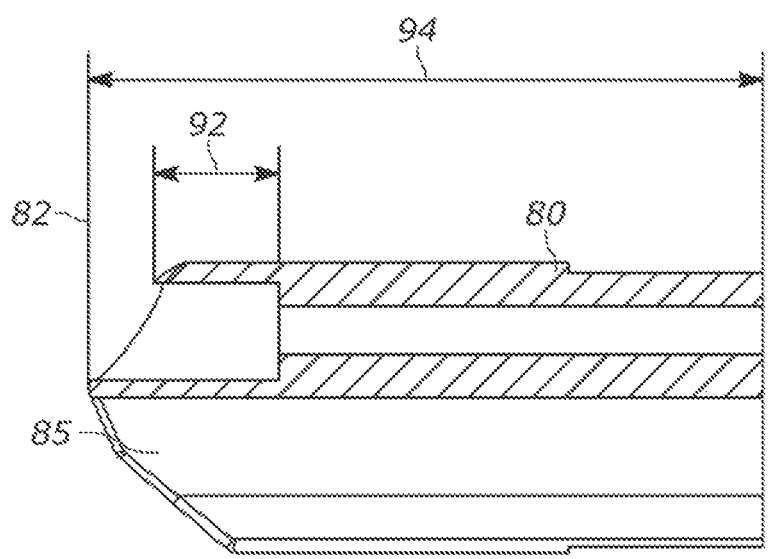
FIG. 9 is a drawing depicting a cross-sectional view of an illustrative example of a distal element for an endoscope.

Distal element 80 includes channel 85. As shown in FIG. 8, channel 85 may be partially open. FIG. 9 depicts a cross-sectional view of FIG. 8 along line A-A. As shown in FIG. 9, distal element 80 includes conduit 82 and channel 85 both of which extend along the length of distal element 80. As can be seen, a geometry of conduit 82 may vary along a length of the distal element. For example, an inner diameter can be varied. An outer diameter of distal element may also vary; for example, as can be seen in FIG. 9, such that it may be fitted to an elongated element. As can be seen in FIG. 9, a face of the distal element 80 is shaped.

Figure 10:
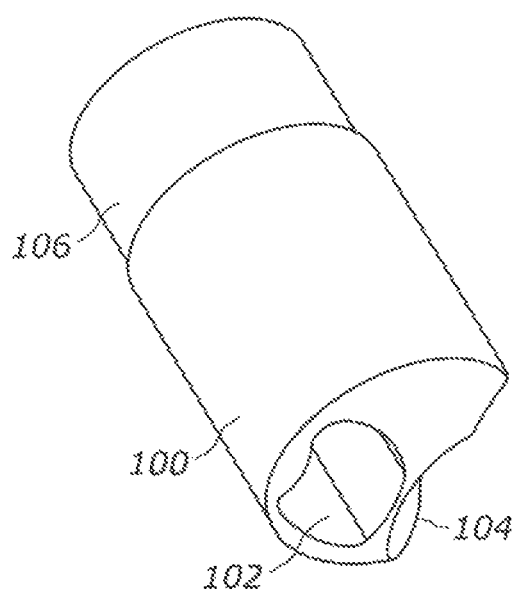
FIG. 10 is a drawing depicting a perspective view of an illustrative example of a distal element for an endoscope.

FIG. 10 depicts a perspective view of an embodiment of a distal element having a single conduit 102 and an open channel 104. Further, it can be seen in FIG. 10, that the outer diameter of the distal element 100 varies its length. Coupling section 106 has a smaller diameter than the rest of the distal element. The coupling section may be constructed in a manner such that it couples to an elongated element.

Figure 11:
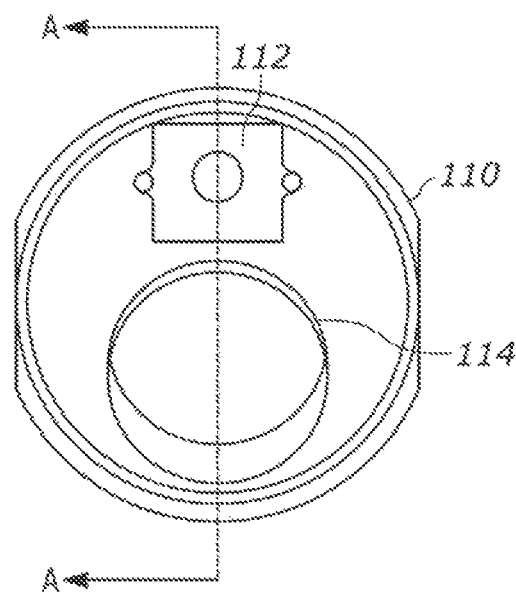
FIG. 11 is a drawing depicting an end view of an illustrative example of a distal element for an endoscope.
Figure 12:
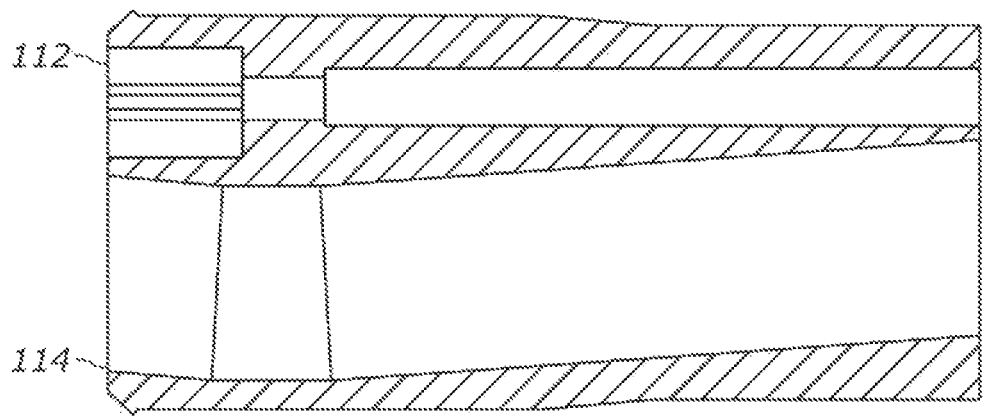
FIG. 12 is a drawing depicting a cross-sectional view of an illustrative example of a distal element for an endoscope.

FIG. 11 depicts an end of distal element 110 having multiple conduits 112, 114. Conduit 114 is cut using a swept cut path. FIG. 12 depicts a cross-sectional view of distal element 110. As can be seen in FIG. 12, a path of conduit 114 varies along a length of the distal element. In particular, the path of conduit 114 moves from an edge of the distal element 110 toward a middle of the distal element 110. A geometry of conduit 112 changes along a length of distal element 110. As can be seen in FIG. 12, a section of conduit 112 has a rectangular geometry and a further section of conduit 112 has a substantially circular geometry. As shown in FIG. 12, an outer diameter of the distal element 110 varies along the length of the distal element.

Figure 13:
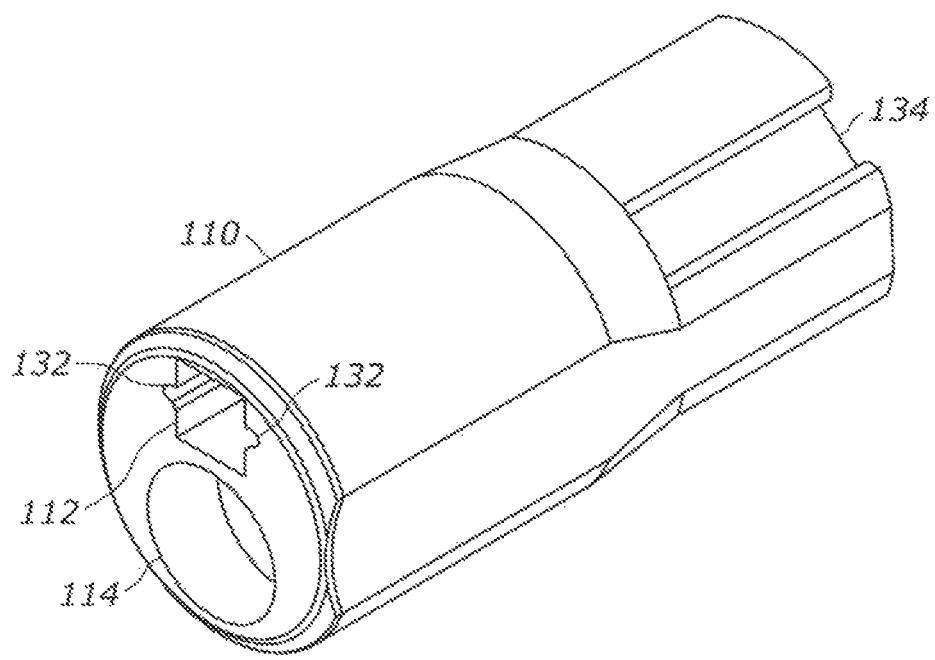
FIG. 13 is a drawing depicting a perspective view of an illustrative example of a distal element for an endoscope.
Figure 14:
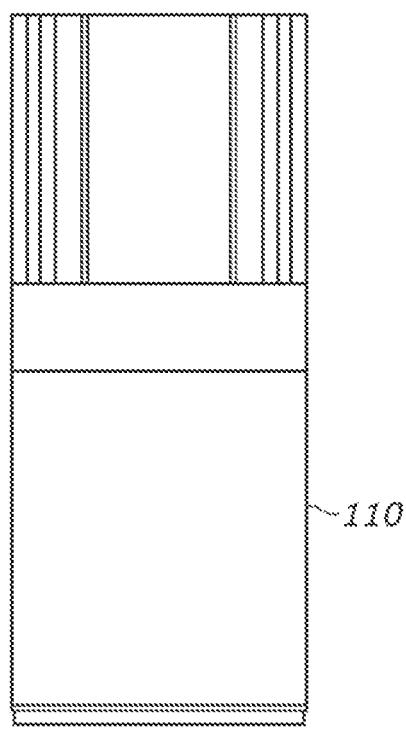
FIG. 14 is a drawing depicting a top view of an illustrative example of a distal element for an endoscope.

FIG. 13 depicts a perspective view of distal element 110 shown in FIGS. 11, 12, 14. As can be seen in FIG. 13, conduit 112 includes cutouts 132. Cutouts may conform a shape of devices, tubing, and/or other elements. In some instances, cutouts may help to elements placed within a conduit. As shown in FIG. 13, an outer diameter and geometry is varied along the length of the distal element 110. Cutout 134 is positioned on an outer surface of distal element 110. In some embodiments, cutout 134 may be designed to couple with an elongated element.

An embodiment may include a cutout designed to house a device such as a sensor, imaging element, light or the like, cable, wire, and/or fiber optic element. FIG. 14 depicts a top perspective view of distal element 110. From this view, the variation of the geometry along the length of the distal element is visible.

Figure 15:
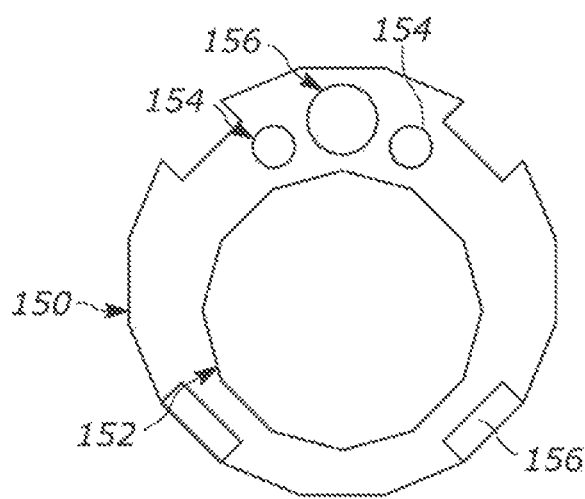
FIG. 15 is a drawing depicting an end view of an illustrative example of a distal element for an endoscope.

As shown in FIG. 15, distal element 150 includes multiple conduits 152, 154, 156 and channels 156. Conduit 152 has a larger diameter that the remaining conduits. Conduit 152 may act as a working conduit. Channels 156 are partially open. In some embodiments, channels that are partially open may house a camera sensor and/or optical fiber.

FIGS. 16-19 depict various views of a distal element constructed using sliced layers. Sliced layer construction may allow for more complicated geometries. Processing limitations of standard construction methods may limit design given size ranges of these elements; thus, it may be desirable to used sliced layer construction and/or additive manufacturing, such as three-dimensional printing. For example, a sliced layer construction process may enable the use of a swept cut path in a conduit of the distal element.

Figure 16:
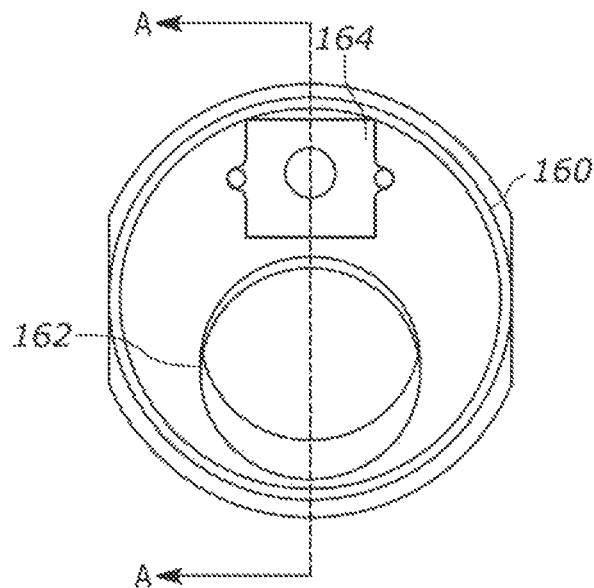
FIG. 16 is a drawing depicting an end view of an illustrative example of a distal element for an endoscope.
Figure 17:
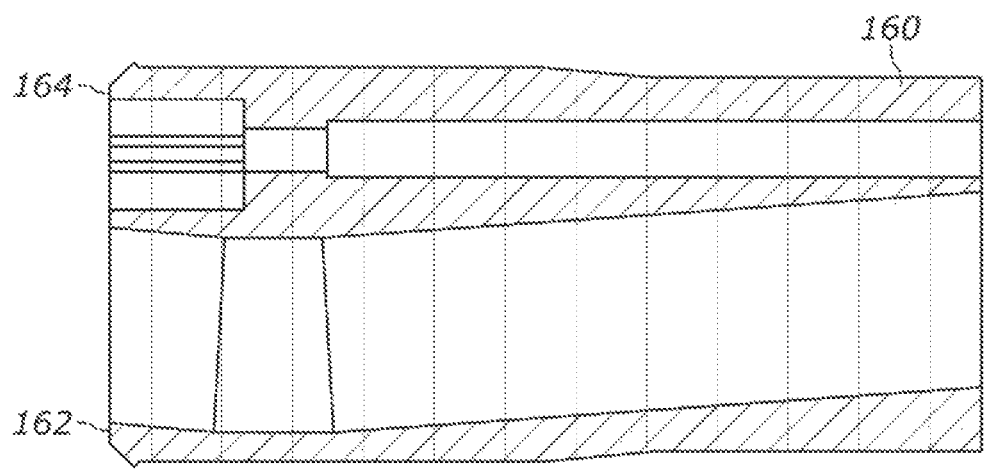
FIG. 17 is a drawing depicting a cross-sectional view of an illustrative example of a distal element for an endoscope.
Figure 18:
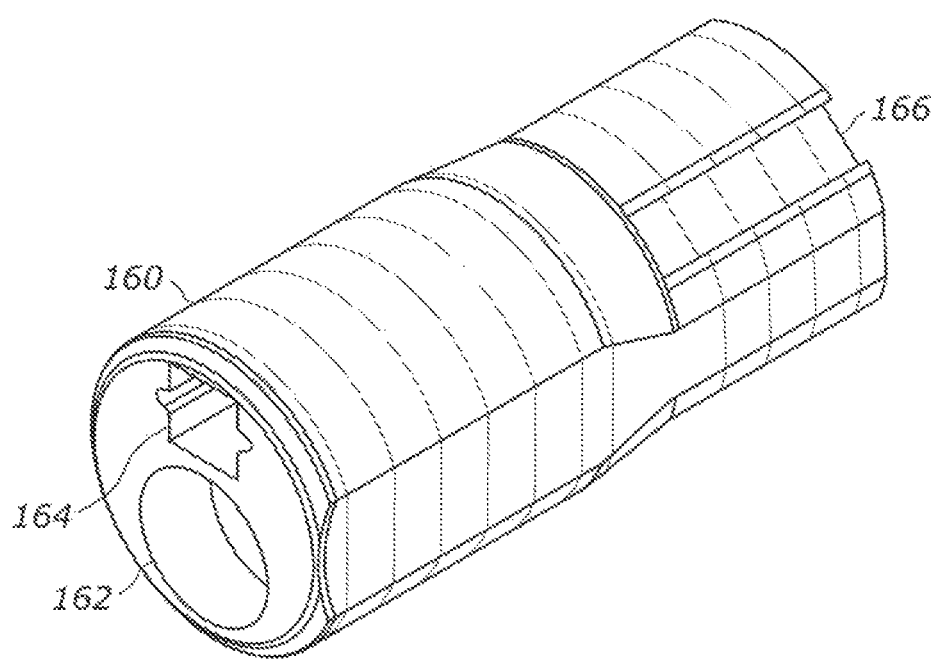
FIG. 18 is a drawing depicting a perspective view of an illustrative example of a distal element for an endoscope.
Figure 19:
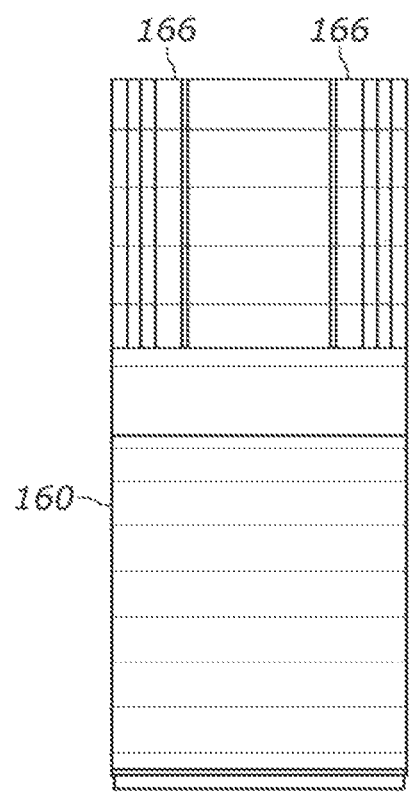
FIG. 19 is a drawing depicting a top view of an illustrative example of a distal element for an endoscope.

As shown in FIGS. 16-17, the sliced layers allow for changing an elevation of conduit 162 along the length of the distal element. Conduit 164 varies in geometry along a length of the distal element 160. FIG. 18 depicts a perspective view of distal element 160. Distal element includes conduits 162, 164, as well as channels 166.

Figure 20:
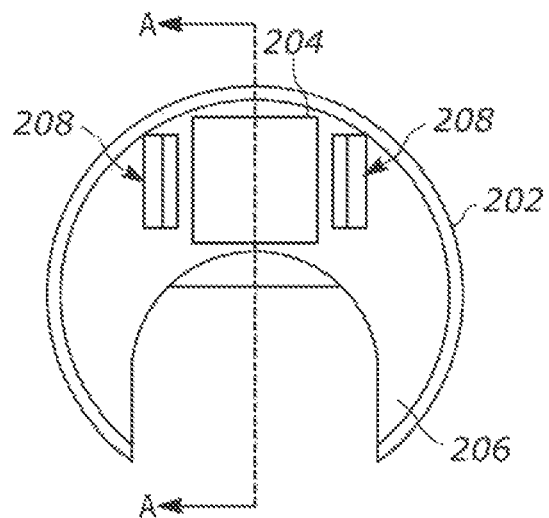
FIG. 20 is a drawing depicting an end view of an illustrative example of a distal element for an endoscope.
Figure 21:
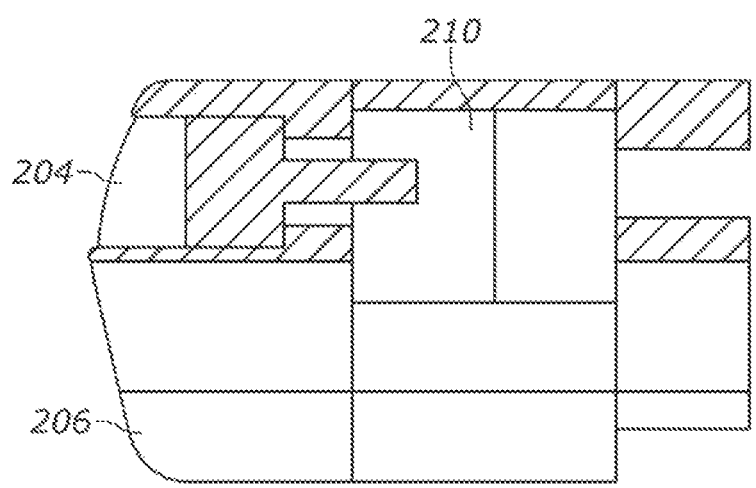
FIG. 21 is a drawing depicting a cross-sectional view of an illustrative example of a distal element for an endoscope.
Figure 22:
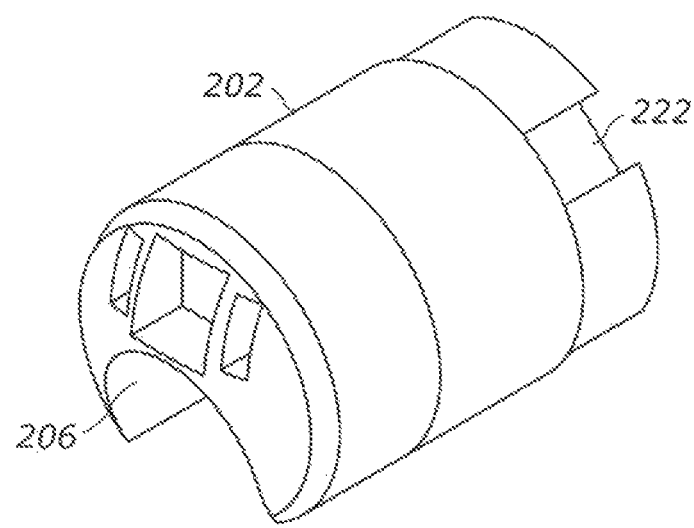
FIG. 22 is a drawing depicting a perspective view of an illustrative example of a distal element for an endoscope.
Figure 23:
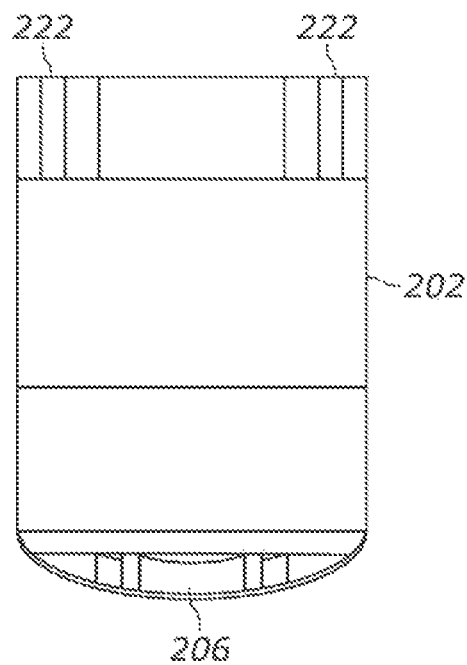
FIG. 23 is a drawing depicting a top view of an illustrative example of a distal element for an endoscope.

As illustrated in FIGS. 20-23, distal element 202 is constructed from multiple sections. Use of multiple sections in the distal element may inhibit undercuts. Distal element 202 includes conduit 204, as well as open channel 206. FIG. 20 shows an end view of distal element 202 which includes channels 208 for lighting elements such as a lightpipe, fiber optic elements, or clear epoxy. FIG. 21 depicts a cross-sectional view of distal element 202 shown in FIG. 20 along line A-A. Light source 210 is positioned proximate to conduit 204 such that the light source provides light to a target area through channels 208. Light source may include but is not limited to Xenon lights, organic light-emitting diode ("OLED") lights, and light-emitting diode ("LED") lights; for example, high lumen LEDs and/or Micro LED lights. FIGS. 22-23 show channels 222 positioned on an outer surface of the distal element 202.

Figure 24:
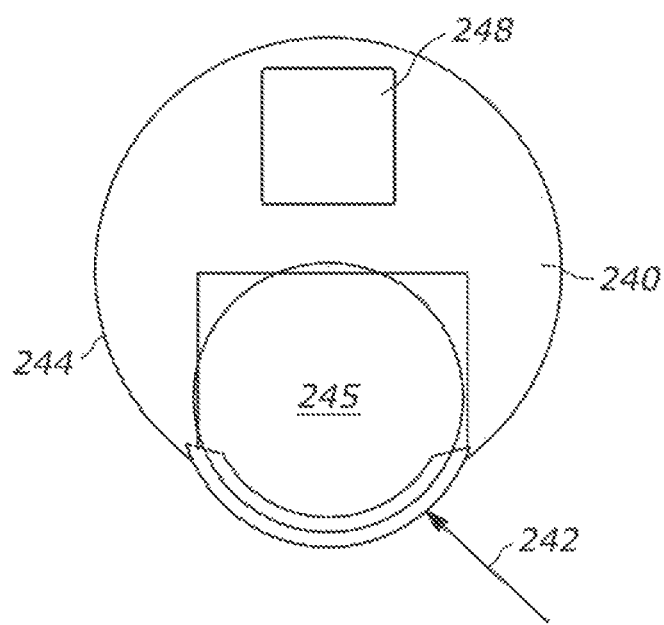
FIG. 24 is a drawing depicting an end view of an illustrative example of a distal element for an endoscope.
Figure 25:
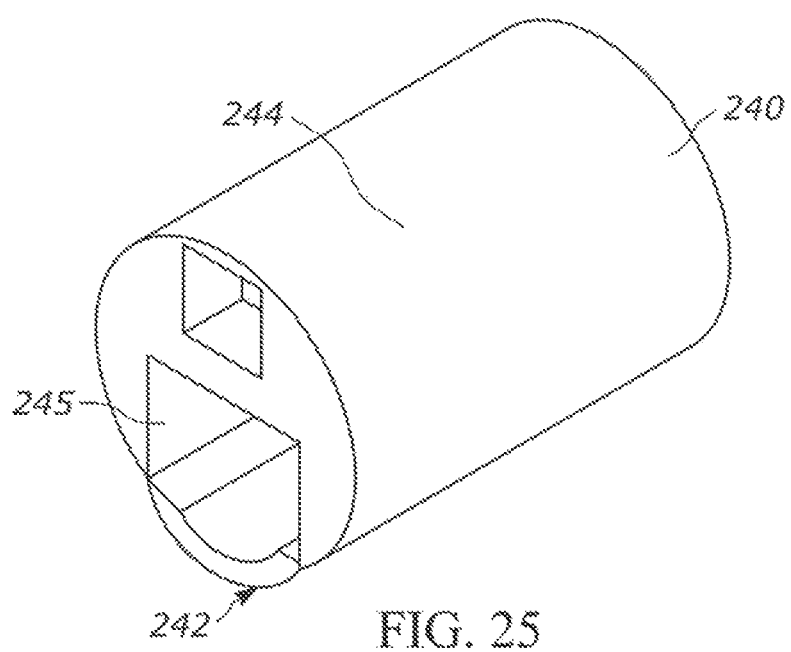
FIG. 25 is a drawing depicting a perspective view of an illustrative example of a distal element for an endoscope.
Figure 26:
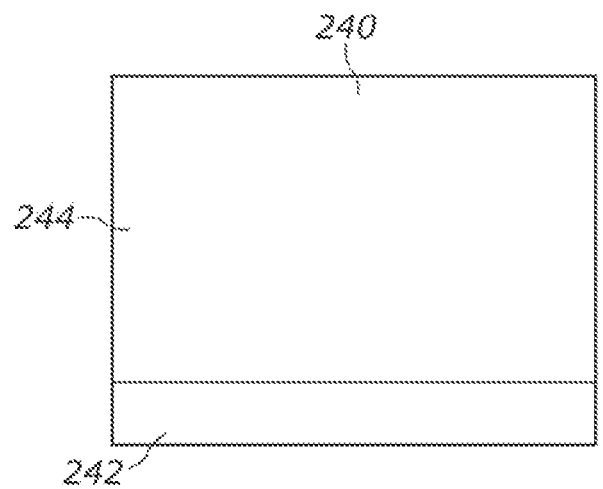
FIG. 26 is a drawing depicting a side view of an illustrative example of a distal element for an endoscope.

FIG. 24 depicts an end view of distal element 240 constructed from flexible member 242 and rigid body 244 which define conduit 245. Conduit 248 is depicted clearly in FIG. 25 which shows a perspective view of the distal element. A side view of the distal element 240 is shown in FIG. 26.

Figure 27:
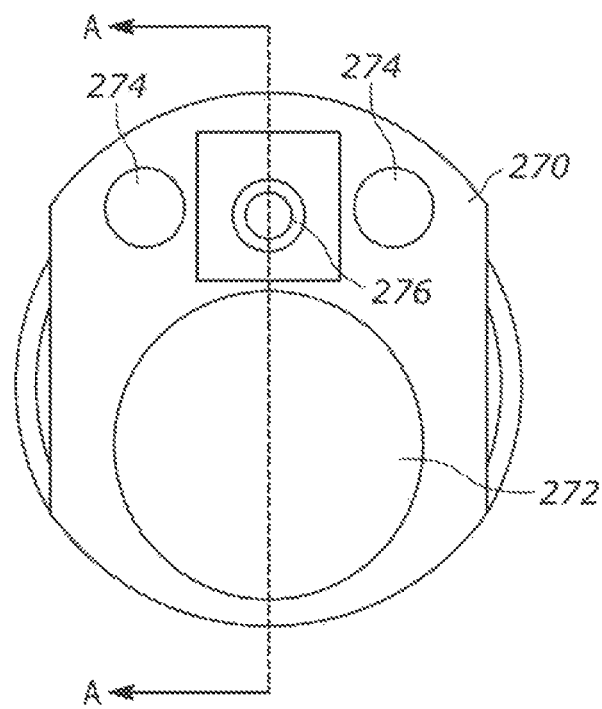
FIG. 27 is a drawing depicting an end view of an illustrative example of a distal element for an endoscope.
Figure 28:
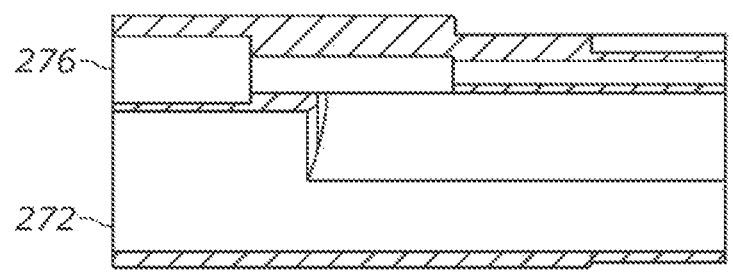
FIG. 28 is a drawing depicting a cross-sectional view of an illustrative example of a distal element for an endoscope.

FIG. 27 illustrates an end view of a distal element having an egg-shaped face. Distal element 270 includes conduits 272, 274, 276. A cross-sectional view of FIG. 27 along line A-A is shown in FIG. 28. Conduits 272, 276 are both shown having varying diameters along the length of the distal element. Conduit 272 may be a working conduit or working channel. In an embodiment, conduit 276 may house an optical sensor.

Figure 29:
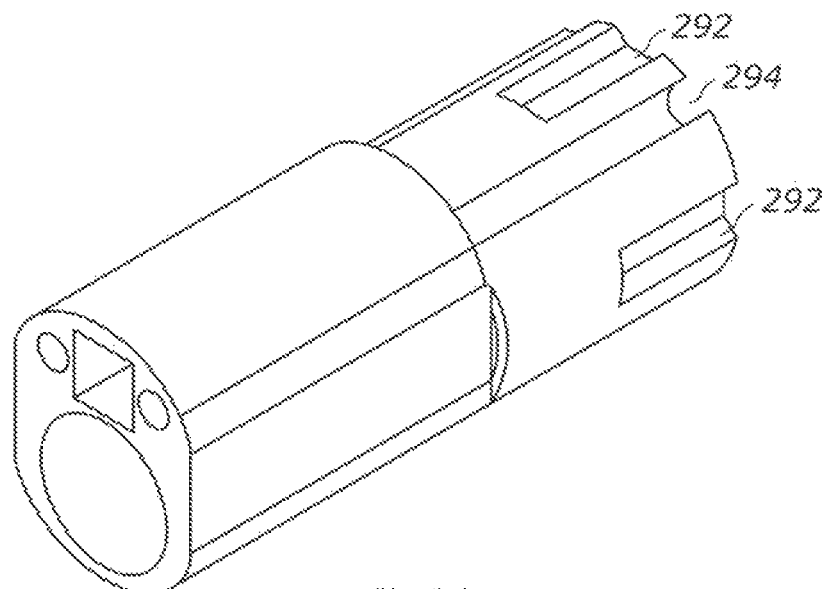
FIG. 29 is a drawing depicting a perspective view of an illustrative example of a distal element for an endoscope.
Figure 30:
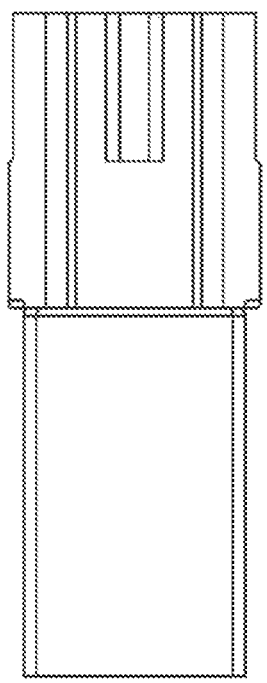
FIG. 30 is a drawing depicting a top view of an illustrative example of a distal element for an endoscope.

FIGS. 29-30 depict a perspective view and a top view of distal element 270, respectively. Channels 292, 294 are positioned on an outer surface of distal element 270. FIG. 30 clearly depicts the varying outer diameter along the length of the distal element.

Figure 31:
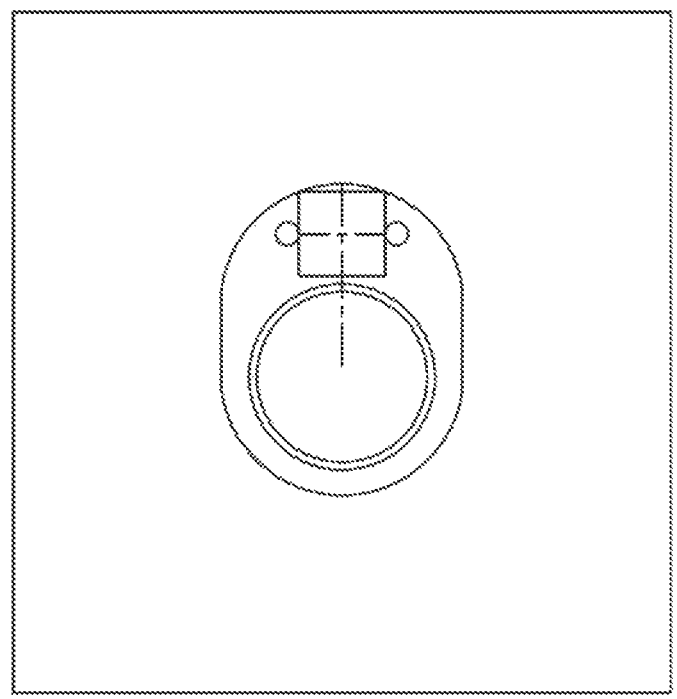
FIG. 31 is a drawing depicting an end view of an illustrative example of an overmold for a distal element for an endoscope.
Figure 32:
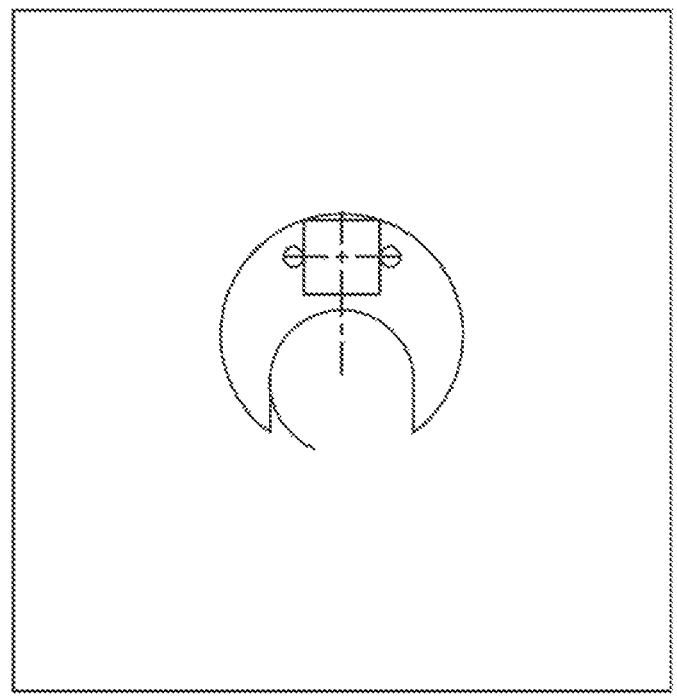
FIG. 32 is a drawing depicting an end view of an illustrative example of an overmold for a distal element for an endoscope.
Figure 33:
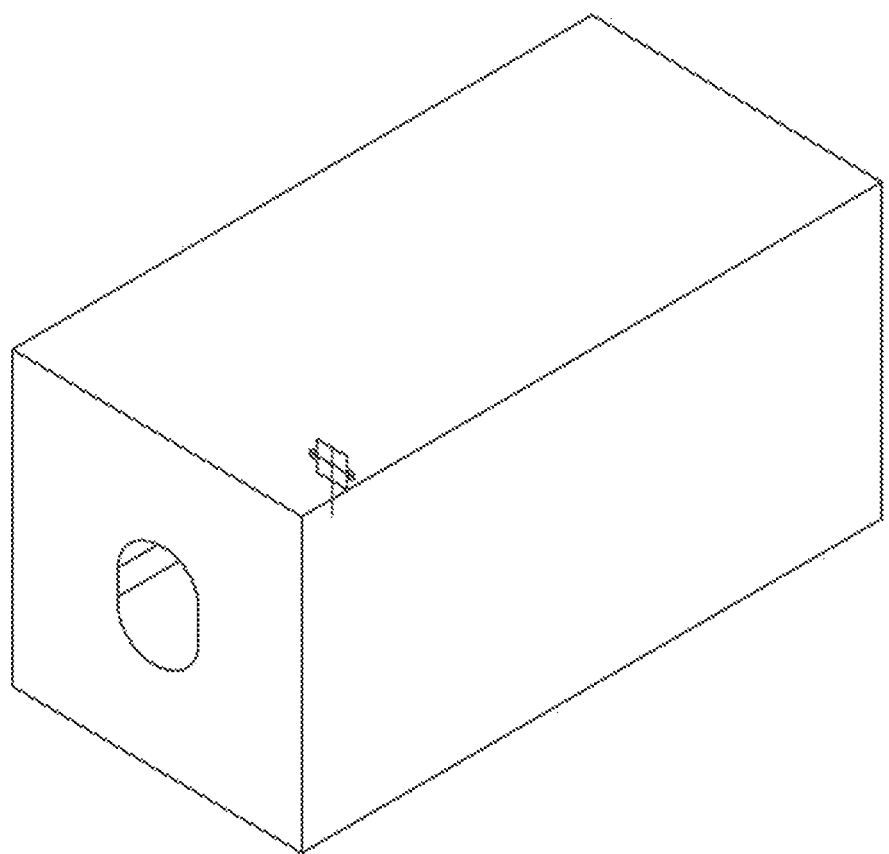
FIG. 33 is a drawing depicting an end view of an illustrative example of an overmold for a distal element for an endoscope.

Overmold drawings reflect a tool necessary to create the distal element. Various configurations were constructed that corresponded to the geometries of the distal element as can be seen in FIGS. 31-33.

As shown in FIG. 9, distal element 80 includes conduit 82 and channel 85 both of which extend along the length of distal element 80. As can be seen, a geometry of conduit 82 may vary along a length of the distal element. For example, an inner diameter can be varied. An outer diameter of distal element may also vary; for example, as can be seen in FIG. 9, such that it may be fitted to an elongated element. As can be seen in FIG. 9, a face of the distal element 80 is shaped.

The scope may include a distal element having openings for additional devices or elements. For example, the distal element may include openings for an illumination element, such as a fiber optic cable, light, and/or light source, and/or an optical element, such as a camera.

An optical element may include a device having a field of view of greater than 60°. In some embodiments, the field of view of the optical element may be greater than 85° or as high as 150 degrees. Further, the depth of field may be as small as 5 mm greater than 15 mm. In some instances, the depth of field may be greater than 20 cm. An optical element such as a camera, for example, a high definition camera or videoscope, may include devices such as, but not limited to, miniature videoscopes.

The distal element may also include openings which may allow for manipulation at a predetermined location, delivery of materials, such as air, liquid, medicines, devices, etc., and/or retrieval of materials, such as tissue, devices, fluids. In an embodiment, the distal element may include an opening which allows for use of suction at a predetermined location and/or a target area.

Elongated elements may couple to both the distal element and the control element. A length of an elongated element may be in a range between 0.5 to 1.5 meters. For example, an elongated element may have a length in a range from about 0.8 to 1.2 meters in some embodiments. An outer diameter of an elongated element may be less than about 4.5 millimeter. In some embodiments, the outer diameter of an elongated member may be less than 4.0 millimeter. For example, an elongated element may have an outer diameter of less than about 3.5 millimeters in an embodiment.

A further illustrative example includes an elongated member and/or shaft having a diameter in a range between 4 mm to 5 mm. A channel extending through the elongated member or shaft may have a diameter in a range from about 2.5 to 3.0 mm. In such an example, it may be desirable to use a camera capable of moving on multiple axes. For example, a camera capable of four-way deflection may be used.

In one illustrative example an elongated member of a scope may have an outer diameter in a range between 4.3 to 4.5 mm and a channel or conduit having a diameter in a range from about 2.8 to 3.0 mm. Such a scope may be utilized for applications where the openings may be larger or the scope requires additional room for additional elements. This may be particularly true for applications involving adults and/or training on devices, such as simulators.

A stiffness of the elongated element may vary along its length. At least a portion of the length may be flexible. In some embodiments, variable stiffness along the length of the elongated element may be created using a stainless steel tube that is laser cut with a variable interrupted spiral pattern. The more cuts, the more material is removed and the more flexible the shaft becomes. Thus, an elongated element may be designed to have a stiffer area proximate to the control element such that torque can be transferred, while being flexible proximate to the distal element such that tight bends can be negotiated and/or patient comfort improved. In an alternate embodiment, the elongated element may include a braided metal section to provide variable stiffness. Another embodiment may include various stiffness of single plastic extrusions brought together through welds to accomplish proper steering, direction, and stiffness.

In some embodiments, a length of a flexible portion of the elongated element may be in a range from about 30 to about 50 millimeters. For example, a flexible portion of an elongated member may have a length in range from about 35 to 45 millimeters. In an embodiment, the length of the flexible portion of the elongated element may be approximately 40 mm.

An elongated element may include one or more conduits. The conduits may have various configurations. For example, the conduits may be coaxial, positioned proximate to each other, and/or positioned on opposite sides of the cross-section of the elongated element. Conduits may include one or more lumen.

Conduits may act as a housing for elements inserted into the elongated element. In some embodiments the elongated element may have one or more conduits configured to receive devices and/or sensors to provide access to a target area.

In some embodiments, conduits may provide a path for materials to reach the distal element and/or a target area. Further, a conduit may be used to transport materials from the target area to the control element or, in some cases, to a position external to the control element.

Elongated element 62 includes conduit 24 running the length of the endoscope elongated element. In some instances, the conduit may slidingly receive instruments, such as nasal endoscope biopsy forceps 70 (See FIG. 5) within the lumen of the conduit and/or allow suction or irrigation.

A working conduit in the elongated element may have an inner diameter of greater than about 2.0 millimeters. Further, the inner diameter of a working conduit may be greater than about 2.1 millimeters in some embodiments.

At least one conduit through the elongated element may have an inner diameter of greater than about 1.3 millimeters. Some embodiments may include conduits having an inner diameter of about 1.4 millimeters or greater.

A sensor array may be used to take measurements throughout a procedure. For example, a sensor array may take distance measurements, for example, the distance that an endoscope has traveled in the body, luminal measurements, such as diameters, lengths, and/or volumes, quantitative changes, physiological measurements within the body, such as temperature, pulse oximetry measurements, etc.

An endoscope may include an elongated element having a flexible section. This flexible section of the elongated element may be constructed from a medical-grade material. In particular, a hydrophobic material may be used. Hydrophobic materials may create a slippery surface which allows the device to be inserted with more ease and/or less discomfort to the patient.

Elongated member 62 of endoscope also includes imaging element 79 and illumination element 36. For example, a high lumen LED or MicroLED may be used to provide light, and a high-resolution video capture device may be used to capture images and/or video in the region of the distal end of the endoscope.

As shown in FIGS. 6 and 34-42, control elements may include any combination of ports, interface elements, and/or indicators. In some instances, an interface element may include a steering element which may control the movement and/or displacement of the distal element and/or optical element of the endoscope. For example, the degrees of deflection from the normal position for the distal element may be greater than 90° in at least one direction. For example, the degrees of deflection from the normal position for the distal element may be 90° in three directions and greater than 90° in a fourth direction. Deflection could be accomplished 180 degrees in all four directions. Deflection may be achieved by pulling or pushing on steering guides, for example, steering wires or pressure sensitive substances.

Interface elements may be positioned on a control element to provide for ease of use of the operator. For example, in some embodiments, interface elements may be positioned along a top surface, a side surface, and/or an underside of the control element. An embodiment of an interface element may act in a joystick-like manner to control movement of the distal element.

Figure 34:
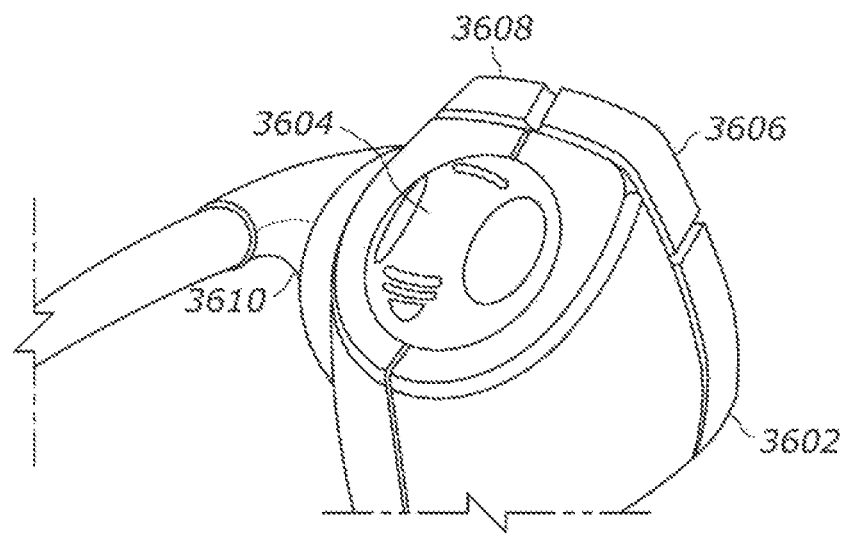
FIG. 34 is a drawing depicting a top perspective view of an illustrative example of a control element for an endoscope.

FIG. 34 depicts a control element 3602 which is designed such that it conforms to the shape of a hand. Interface element 3604 is controlled in a manner similar to a roller ball for ease of use. Further, interface elements 3606, 3608, may control audio recording and image capture, respectively. In some embodiments, interface element 3606 may control audio recording and transcription. These interface elements may have multiple settings. For example, a quick press may take an image or record a predetermined amount of audio, while pressing and holding these elements may activate video recording or extended audio recording. Further, the interface elements may be programmed to initiate auto-reporting data to one or more reports, databases, or processors. Data may include, for example, audio, visual, positioning, and temporal data, as well as physical and physiological measurements. This data could potentially be transmitted wirelessly from the endoscope to a computer at a remote location.

Figure 35:
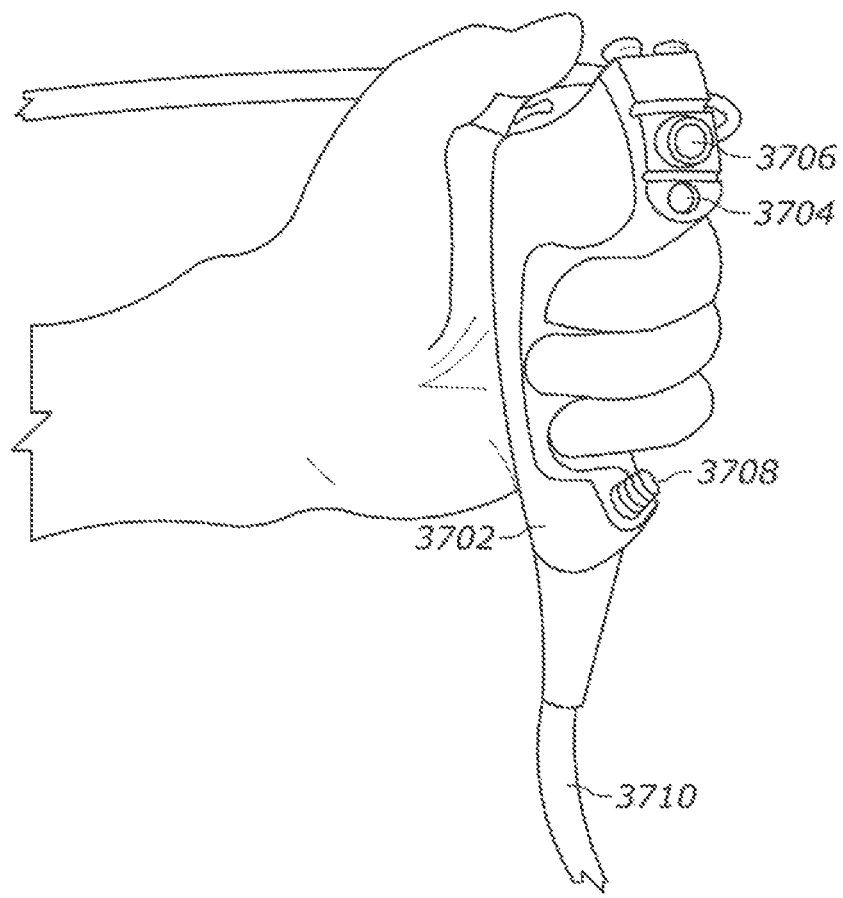
FIG. 35 is a drawing depicting a front perspective view of an illustrative example of a control element for an endoscope.

In some instances, the functionality of the interface elements may be programmable by a user for ease of use. In alternate embodiments, the functionality of the interface elements may be defined by a use of the device. For example, when then endoscope device is used to monitor a feeding tube the needs may be different from when the endoscope device is used to conduct a TNE. FIG. 35 depicts a front perspective view of control element 3702 which conforms to the shape of a hand. As can be seen in FIG. 35, ports 3704, 3706 may be positioned such that they do not interfere with the interface elements and the user's ability to control aspects of the endoscope. For example, port 3704 serves as a connection point for suction while port 3706 allows for a connection of fluids, in particular, air and/or water. Port 3708 provides access to a conduit and/or channel that runs through elongated element 3710.

In some embodiments, the control element may include multiple ports. At least one port may provide access to a channel and/or conduit within the elongated member. An insertion element, for example an instrument may be inserted into a conduit of the elongated element using a port. Further, an instrument may be coupled to a control element at a port which provides access to a conduit and/or channel within the elongated element. An insertion element may include, but is not limited to an instrument, such as forceps, in particular, biopsy forceps, a feeding tube, a cable for sensors, sensors, accessory, illumination elements and/or optical elements. Further, interface elements may be positioned on a control element such that it provides easy maneuverability of the distal element.

In some embodiments, after positioning an instrument within the elongated element, the control element may be removed. Wires and/or connectors to various elements, for example, audio and imaging elements, sensors, and the like may remain so that these elements can be used.

Figure 36:
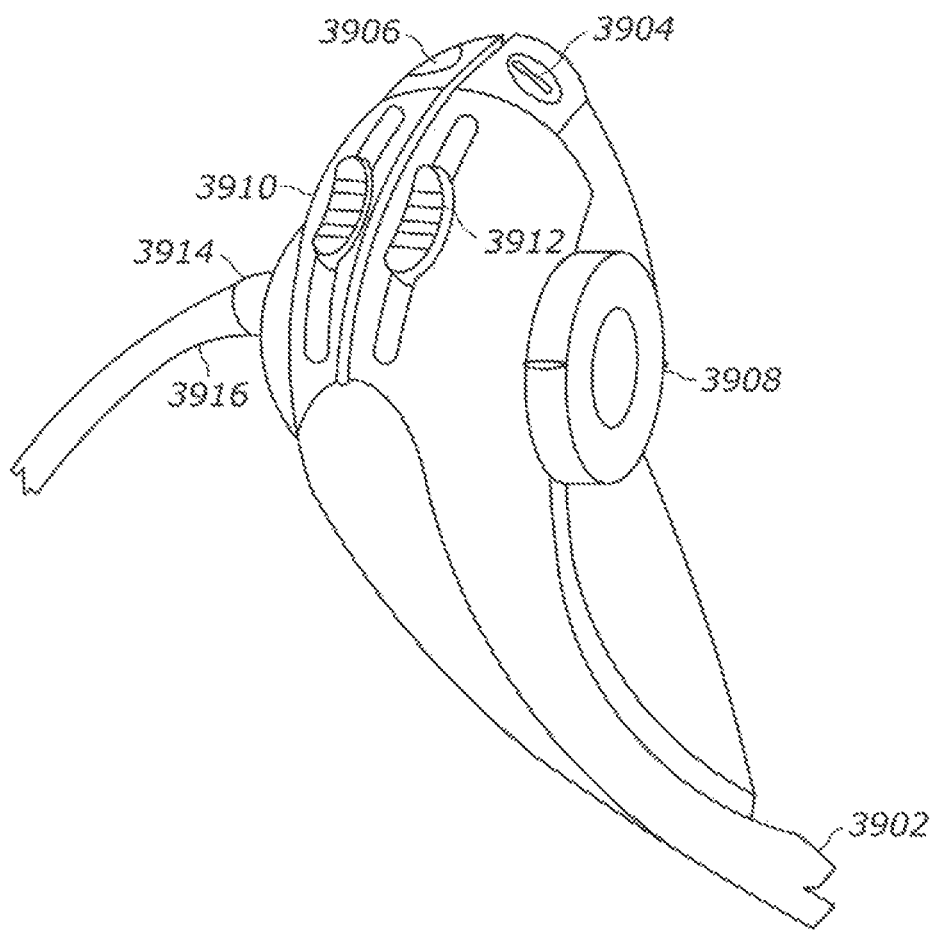
FIG. 36 is a drawing depicting a top perspective view of an illustrative example of a control element for an endoscope.

FIG. 36 depicts a rear view of a further embodiment of a control element. Control element 3902 includes interface elements 3904, 3906, 3908, 3910, 3912. Port 3914 connects to line 3916 which may connect to a computer control element, a display, and/or a computer. In some instances, port 3914 is used to provide suction, air, and/or water, as well as house electronics. Interface element 3906 may be used to actuate photo or video capabilities of the endoscope, while interface 3904 may be used to control audio input. Interface elements 3910, 3912 may be used to control movement of the distal element, for example, via a steering collar (shown in FIGS. 7A-B) in part. Interface element 3908 controls an amount and/or duration of fluid provided to a target area via the endoscope. For example, interface element 3908 may be programmed to deliver predetermined amount of fluid over a predetermined time frame. These settings may be controlled by a user and/or by protocols designed for each use of the endoscope. In particular, a short twist of interface element 3908 may deliver 5 mL bursts of water to the target area.

Figure 37:
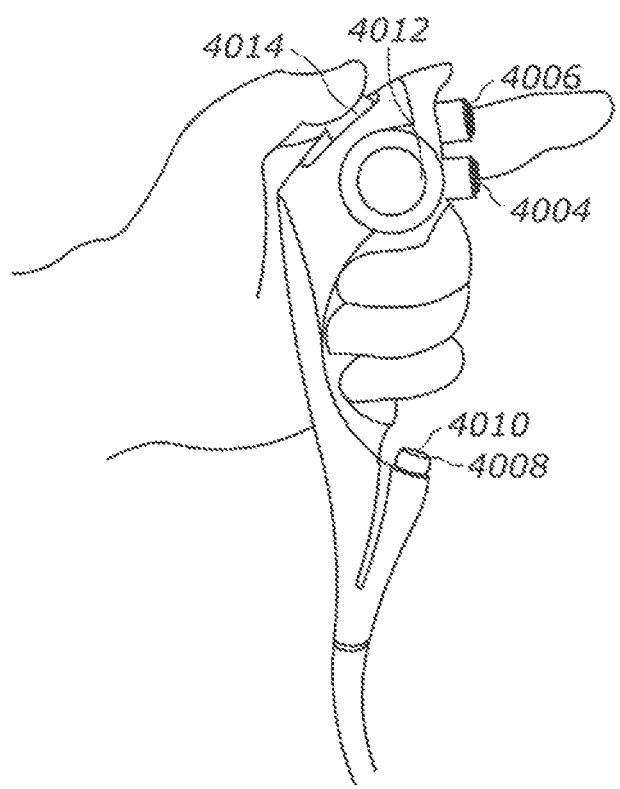
FIG. 37 is a drawing depicting a side perspective view of an illustrative example of a control element for an endoscope.

FIG. 37 depicts a side view of control element and illustrates the ergonomic design of the control element. Port 4006 provides a connector for suction, so that suction can be provided to a target area. Port 4004 provides a connection for fluids which may be delivered to a target area. An amount of fluid and/or type of fluid may be controlled using the interface element 4012. Interface element 4014 controls the positioning of the distal element. Port 4008 provides access to the target area via a conduit running through the elongated element for insertion element 4010.

In some embodiments, there may be a scope-stiffening element to allow use of the endoscope in aerodigestive medicine. For example, a wire may be used as a stiffening element in the elongated element.

Additional interface elements may be used to control various aspects of the device. For example, foot pedals may be used to activate and control fluid flows and/or suction, control imaging devices and/or audio devices. Input devices capable of providing information to the various systems may include interface elements, for example, buttons, joysticks, tracker balls, foot pedals, virtual reality devices, goggles, glasses, and the like, sensors, imaging elements, audio elements, and/or any device configured to report a value.

In some embodiments, an interface element may be programmed to interact with a specific a behavior of the operator to achieve a desired outcome. Thus, it may be possible to customize the inputs based on the needs and/or desires of a user and/or a use. For example, some users may prefer a specific configuration of interface elements that combine input from one or both hands and/or one or both feet. Further, some protocols may require specific movements from a user that may make it desirable to alter the inputs so that the user has an increased ability to use their hands for other purposes.

As discussed herein, the elongated element 4107 has a conduit running the length of the endoscope and is adapted to slidingly receive an inserted element, such as biopsy forceps, through port 4106 and into a lumen of the conduit. Control element 4102 also includes port 4110 for connecting to the computer control unit, a computer and/or a display. Ports 4112, 4114 may be configured to deliver fluids and/or such to a target area via the endoscope.

Figure 38:
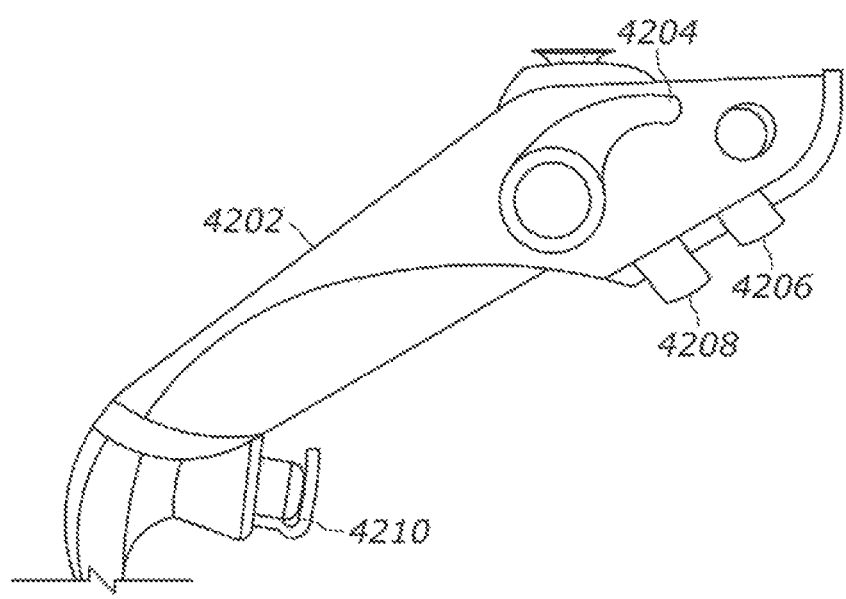
FIG. 38 is a drawing depicting a side perspective view of an illustrative example of a control element for an endoscope.

FIG. 38 depicts a side view of a further embodiment of a control element 4202. Interface elements 4204 may be used to control what is occurring at a target area. Ports 4206, 4208, 4210 may be used to provide inputs and/or remove materials to target areas.

Figure 39:
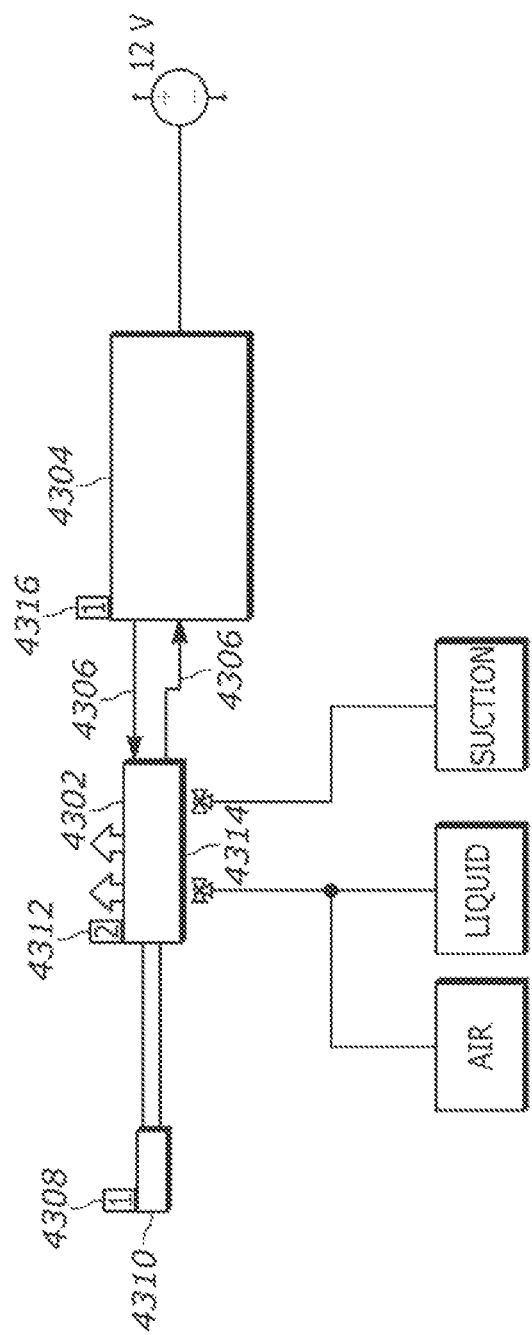
FIG. 39 is a block diagram depicting a system that incorporates an endoscope.

As shown in FIG. 39, control element 4302 may be connected to a computer control element 4304 via cables 4306. Further, the control element may be connected to a computer and/or a display. FIG. 39 depicts positions for a light source for use with the endoscope. In some embodiments, light source 4308 may be positioned proximate to and/or in distal element 4310. A light source 4312 may also be positioned in control element 4302. Further, light source 4316 may be positioned on computer control unit 4304. Regardless of the position, light may be provided to an illumination element positioned on distal element 4310 using optical fiber or LED of MicroLED.

The computer control element may be designed to sit on a bench. The size of the computer control element may be less than thirty centimeters by 16 centimeters by 10 centimeters. In some cases, the computer control element may be designed to be portable for easy transport.

Figure 40:
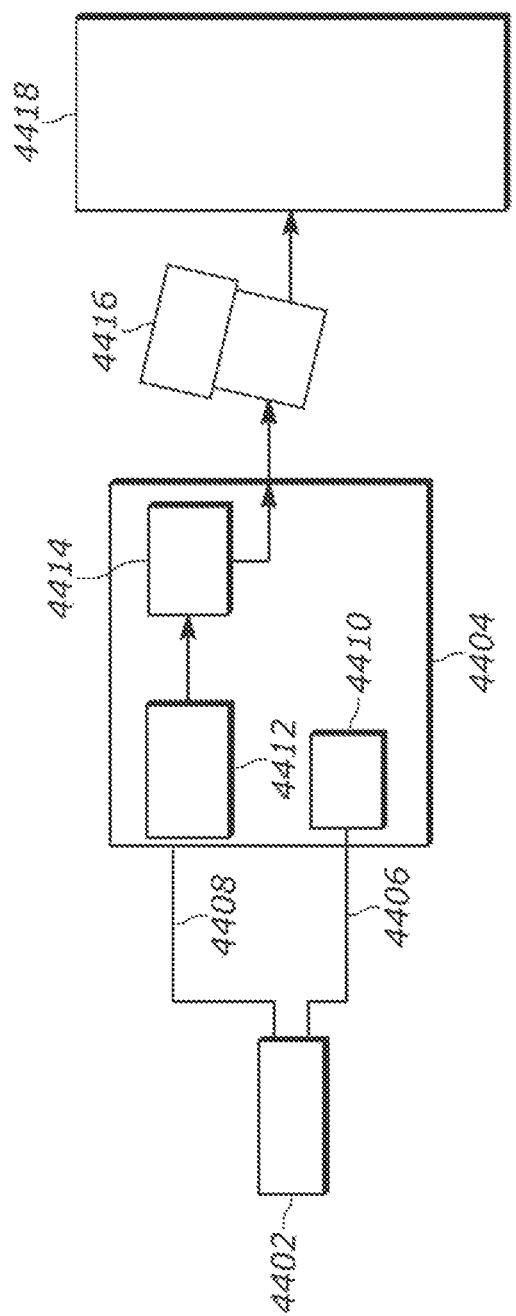
FIG. 40 is a block diagram depicting a system that incorporates an endoscope.

As is shown in FIG. 40, endoscope 4402 may be connected to computer control element 4404 using cables 4408 and optical fiber 4406. In particular, optical fiber 4406 may connect light source 4410 in the computer control element 4404 with illumination elements positioned on the scope.

Images captured on the imaging element may be displayed using a computer connected to the computer control element. FIG. 40 depicts an illustrative example of a system including endoscope 4402 coupled with a computer control unit 4404 that includes multiple drivers 4412, 4414. In particular, an optical element controller 4412 is positioned within the computer control element 4404. Data may be transmitted from the optical element controller 4412 to computer 4416 and/or display 4418. In addition, processor 4414 may alter data from the optical element controller prior to providing it to the computer 4414.

Figure 41:
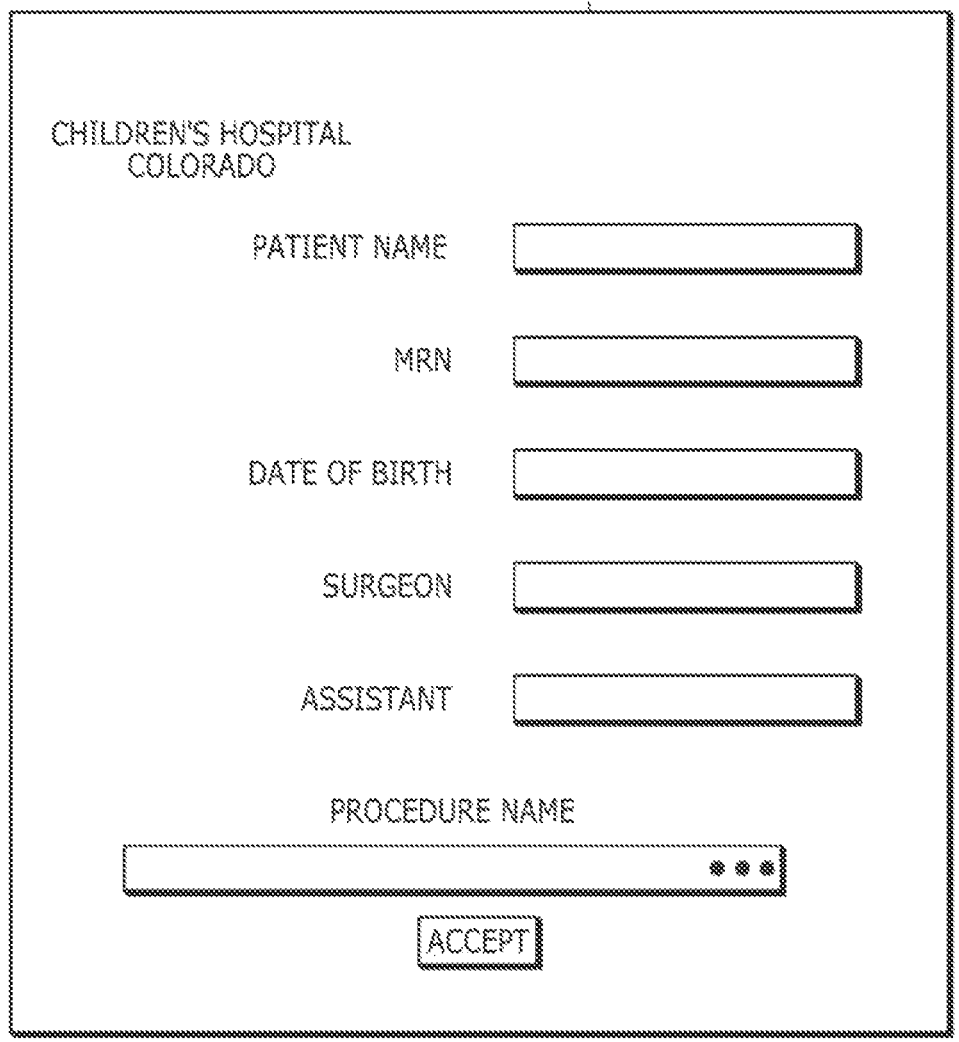
FIG. 41 is a screenshot of a setup display for the system.

During a procedure, a screen connected to the computer will be controlled by software such that information and/or images related to a patient and/or procedure are displayed on the screen. As shown in FIG. 41, software may have a setup form 4500 which shows up on a display. Fields on the setup form may vary according to the requirements of the physician, hospital and/or procedure.

Figure 42:
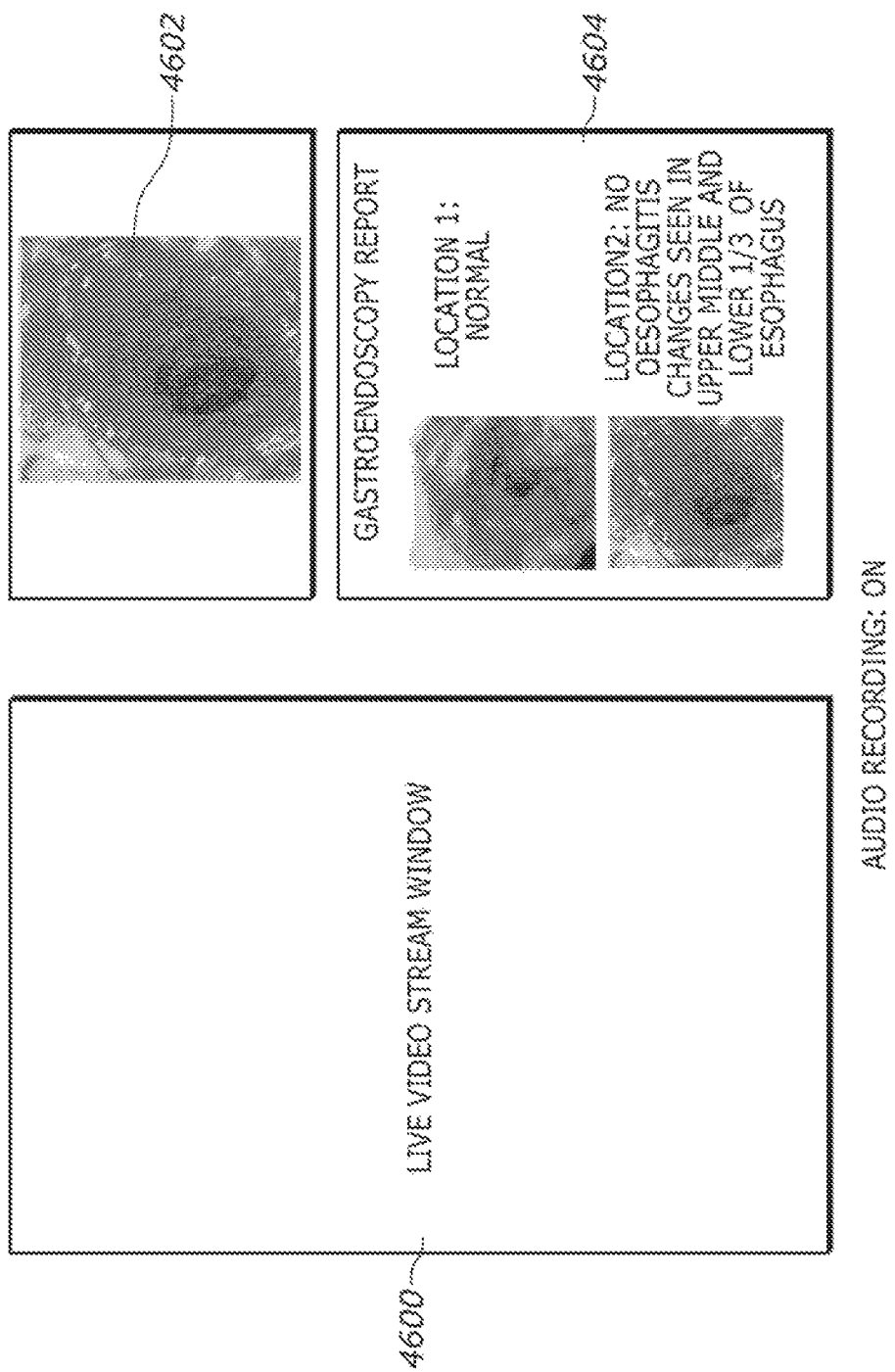
FIG. 42 is a screenshot of a working display for the system.

Images, forms and/or reports may be generated by the computer from one or more inputs from a program, a user, an audio element, an imaging element and/or sensors. The computer may follow a predetermined algorithm that displays various images depending on the type of procedure performed. For example, FIG. 42 depicts a display for use during a procedure which shows live stream video 4600, a static image 4602 and/or report 4604 These fields may be determined by an end-user, such as a physician, a hospital or the like. Using the computer, the system may be designed to auto-report. In some instances, this may occur based on a predetermined time interval, movement interval and/or event. Further, auto-reporting may be controlled by an end-user.

Figure 43:
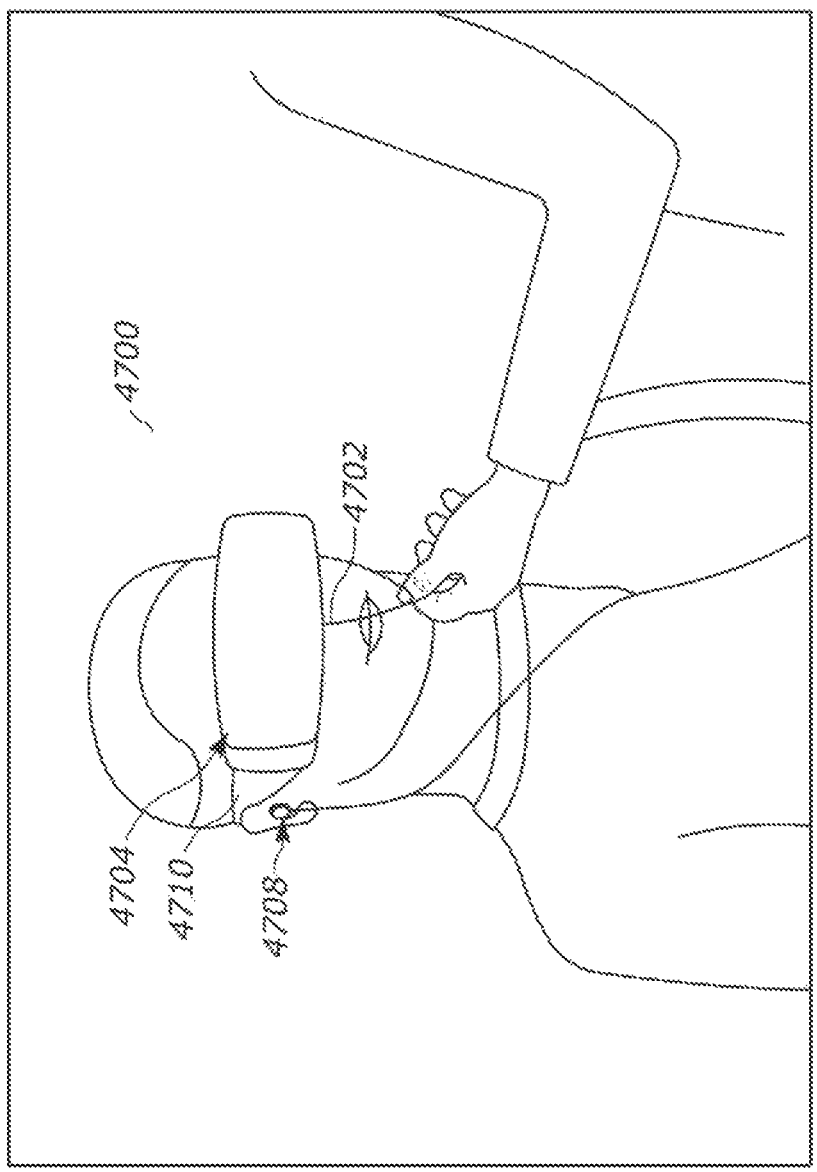
FIG. 43 is a depiction of an exemplary distraction device.
Figure 44:
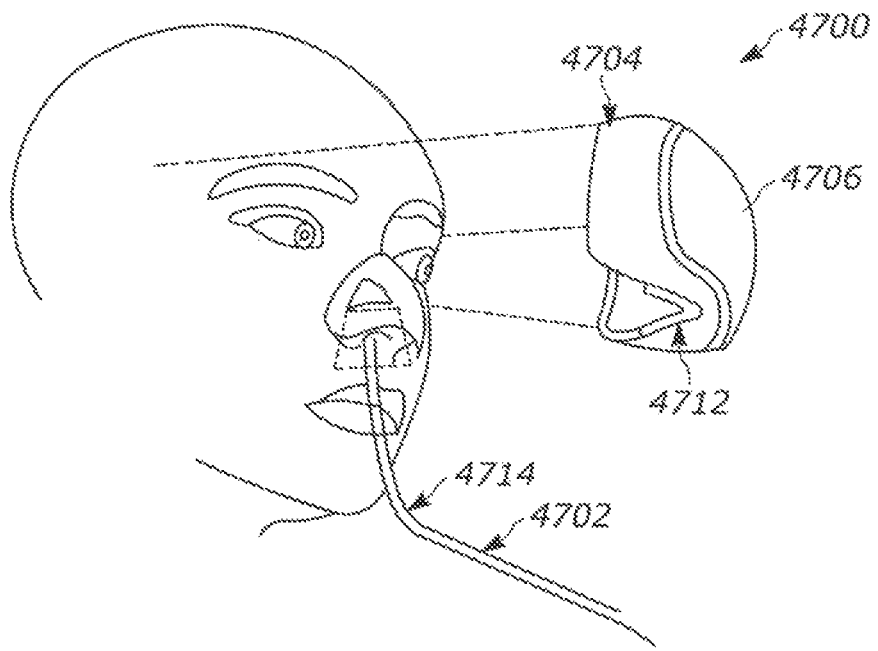
FIG. 44 is another depiction of an exemplary distraction device.

FIGS. 43 and 44 depict a disassociation (or distraction) device 4700 that may be incorporated into any of the previously discussed endoscope or scope systems. In this exemplary embodiment, the disassociation device 4700 is used in connection with a trans-nasal endoscope 4702. The disassociation device 4700 may be used to create a dissociative experience between the patient and the doctor while a patient is undergoing an unsedated endoscopic, or other, procedure. Specifically, the disassociation device 4700 assists in distracting the patient from any discomfort, pain, anxiety or fear during the procedure while also allowing the doctor to focus on the procedure itself. For trans-nasal endoscopic procedures specifically, without use of the disassociation device 4700, the patient often makes eye contact with or otherwise distracts the doctor during the procedure, which may result in a more difficult and lengthy procedure, and even sometimes a less successful procedure. Thus, the dual benefit of the disassociation device 4700 (i.e. distracting and disassociating the patient from the procedure and allowing the doctor to focus on the procedure itself and removing his/her fear of performing an unsedated procedure) may make endoscopic procedures easier and more successful for both the patient and the doctor.

In this embodiment, the disassociation device 4700 is in the form of goggles 4704 that are placed over a patient's eyes to partially or fully occlude the patient's view of the procedure and other outside distractions. In addition, the goggles 4704 may include one or more screens 4706 that can display various videos to distract the patient during the procedure, such as a movie, television show, video game or other video clip, images, text, designs, emojis, etc. One particularly interesting benefit and advantage that can be advanced with the goggles 4704 and the screen 4706 is an immersive experience that can fully distract and disassociate the patient from the procedure. In the context of a child undergoing a trans-nasal endoscopy, the child patient can be immersed in a story or environment from the night before the procedure until the end of the procedure. For example, the child may start reading, watching, or listening to a story the night before the procedure that culminates in a show or other video on the screen 4706 of the goggles 4704 during the medical procedure. Such a immersive experience can fully disassociate the child from the procedure, thereby putting less stress on the child and making the procedure easier and more successful.

The screen 4706 may be made of a variety of visual display components, including but not limited to liquid crystal displays (LCDs), light-emitting diode LCDs (LEDs), and Micro LEDs, or any other suitable visual display. The disassociation device 4700 may also utilize headphones 4708 (wired or wireless) or some other sound-producing device such as an electroacoustic transducer or speakers so that the patient can also be distracted by the audio component of any audiovisual distraction playing on the screen 4706 of the goggles 4704. Alternatively, instead of using a disassociation device 4700 with built-in screen 4706, a phone or other similar device may be placed within the goggles 4704 and used as the display for the visual distraction. Due to the short distance between the screen 4706 and the user's eyes, one or more lenses may be incorporated in the goggles 4704 to allow the user to focus on the screens without issue. The disassociation device 4700 may be attached to the patient's face of all ages from children to adults using a variety of methods known in the art, such as with an elastic strap 4710 as shown in this embodiment. Specific attachments and shapes of the goggles to this elastic allow this device to attach to individuals of pediatric and adult ages while accomplishing transnasal endoscopy with easy nasal access.

The screen 4706 may be used in an interactive manner with the patient to cue the patient to move, adjust, turn, or angle the patient's head a desired by the examiner or provider in order to facilitate an efficient, effective, and successful procedure. For example, the screen 4706 may be displaying a movie during the procedure where the entire movie is in full view such that the patient can fully observe the display on the screen 4706 and the patient's gaze remains fixed and directed to the center of the display on the screen 4706. If the procedure requires the patient to move or adjust, such as to look up or move their head upwardly, the display on the screen 4706 (automatically or upon manipulation by the examiner or provider) may be "moved" such that the display on the screen 4706 is only partially viewable up and out of view of the patient's prior gaze such that the patient only sees the bottom half of the display on the screen 4706. In order to see the entire display on the screen 4706 the patient looks or moves their head up in the "direction" of where the display has moved and upon moving the appropriate amount the screen 4706 will re-center the display to the patient's adjusted gaze. The same process can be used to motivate or encourage the patient to turn left, right, or angle the head as desired. Some prior art may describe a 3D game or avatar in such an environment in which a patient interacts with the environment. The system described herein is uniquely different in that the examiner is able to control the immersive environment for the patient, which enable the adjustment of the seated medical position of the patient to more safely and effectively perform the procedure.

Figure 45:
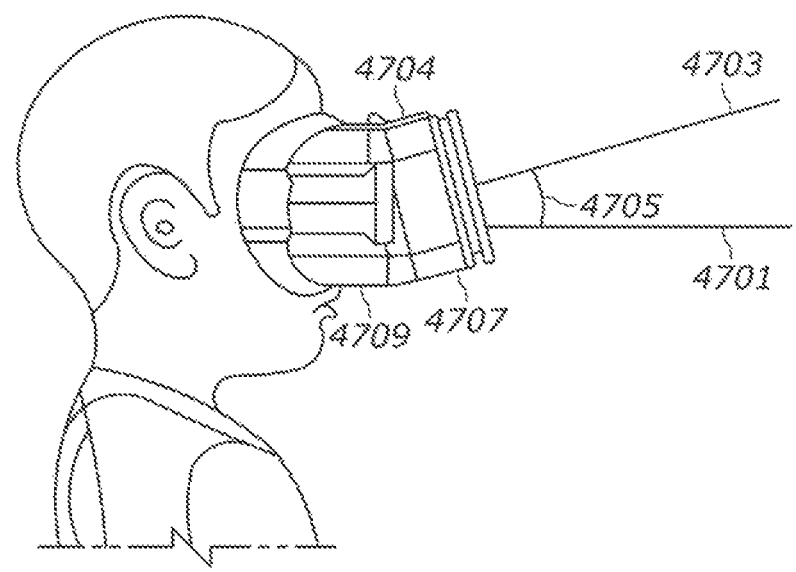
FIG. 45 is a side view of an exemplary distraction device.

When the disassociation device 4700 is used with the trans-nasal endoscope 4702, the nasal passageways of the patient should be exposed so that the physician has full access and the patient properly positioned in a sitting still position with ability to communicate and interact with the physician. Prior art virtual reality or similar display-based goggles generally cover all or a portion of the nose, thereby making access to the nasal passageways as necessary for trans-nasal endoscopy difficult or impossible. Thus, in the embodiment shown in FIG. 45, the goggles 4704 are designed to enable unimpeded access to the nasal passageways while interacting with provider to maintain proper seated positioning. Specifically, the screens 4706 (and any lenses provided in the goggles 4704) of the goggles 4704 are not aligned directly with the patient's neutral or natural line of sight 4701. Instead, the goggles 4704 have a distal portion 4707 that is angled upward from the main, proximal portion 4709 such that the patient has an elevated line of sight 4703. This distal portion 4707 is disposed at an upward angle with respect to the main, proximal portion 4709 of the goggles 4704 to provide clear access to the nasal passageways of the patient such that a trans-nasal endoscopy can be performed without issue. The angled design also helps limit various risks that would increase if the physician didn't have unimpeded access to the nasal passageways, including the risk of turbinate damage, septum damage, increased risk of nose bleed/epistaxis, adenoid damage, sinus damage, potential of cribriform plate damage and injury to brain, increased pain from scope in wrong direction, and increased damage with early nasal endoscopist due to poor technique. In this exemplary embodiment the angle 4705 between the patient's neutral line of sight 4701 and elevated line of sight 4703 can range anywhere between 5-25 degrees and preferably is 15 degrees. However, this angle 4705 can vary further outside this range so long as the angle 4705 enables better access to the nasal passageways and does not cause too much strain on the user's eyes. In addition, the goggles 4704 may have a carved-out portion 4711 (see FIG. 46) that further ensures unimpeded access to the nasal passageways while a user is wearing the goggles 4704.

The disassociation device 4700 may also include a distance sensor 4712. In this embodiment, the distance sensor 4712 is integrated into the nosepiece of the goggles 4704, although the distance sensor 4712 may be utilized with the disassociation device 4700 in a variety of ways. The distance sensor 4712 may be used in connection with the trans-nasal endoscope 4702 to provide information on the position of the trans-nasal endoscope 4702 during a procedure and may interpret body cavity luminal pressuring-sensing capabilities of the endoscope. The distance sensor 4712 may detect the position of the trans-nasal endoscope 4702 in a variety of ways. In the embodiment shown in FIGS. 43 and 44, the trans-nasal endoscope 4702 may include measuring marks 4714 spaced along the length of the trans-nasal endoscope 4702. These marks 4714 may be spaced an equal distance apart. As the trans-nasal endoscope 4702 is advanced into a patient's body, the distance sensor 4712 detects the presence of each mark, thereby indicating that the trans-nasal endoscope 4702 has advanced a certain distance into the patient's body, as determined by the distance between each measuring mark 4714. In one embodiment, the distance sensor 4712 is a magnetic, or hall-effect sensor, and the measuring marks 4714 are made of a metallic material detectible by the hall-effect sensor. In another embodiment, the distance sensor 4712 is a light sensor and the measuring marks 4714 either emit light or are made of a different, reflective material than the remainder of the endoscope 4702 that is detectible by the light sensor. In yet another embodiment, the distance sensor 4712 is a mechanical sensor and the measuring marks 4714 are raised bumps or lines that are detectible by the mechanical sensor.

While in this embodiment a distance sensor 4712 is incorporated into the goggles 4704, a variety of other sensors may also be incorporated into the goggles 4704. This includes sensors that are capable of detecting a variety of a patient's vital signs, including but not limited to heart rate, pulse oximetry, blood pressure, sweat content, carbon dioxide and other gasses' exhalation levels, temperature of the human body, exhalation sounds and respiratory rate, skin elasticity, ocular pressure, pupil sizes and distances, tympanic membrane compliance, hearing aid function, atmospheric temperature, gas content, and interpretation of endoscopic transmission of luminal pressure readings from body cavities. In addition, sensors integrated into the goggles 4704 may be used in a variety of other medical procedures.

Figure 46:
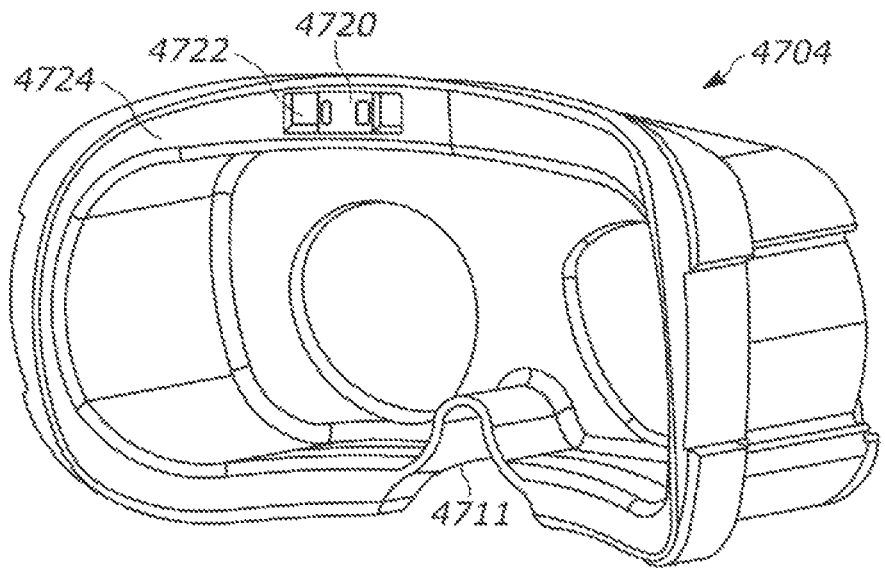
FIG. 46 is a view of an exemplary distraction device depicting an optional integrated sensor.
Figure 47:
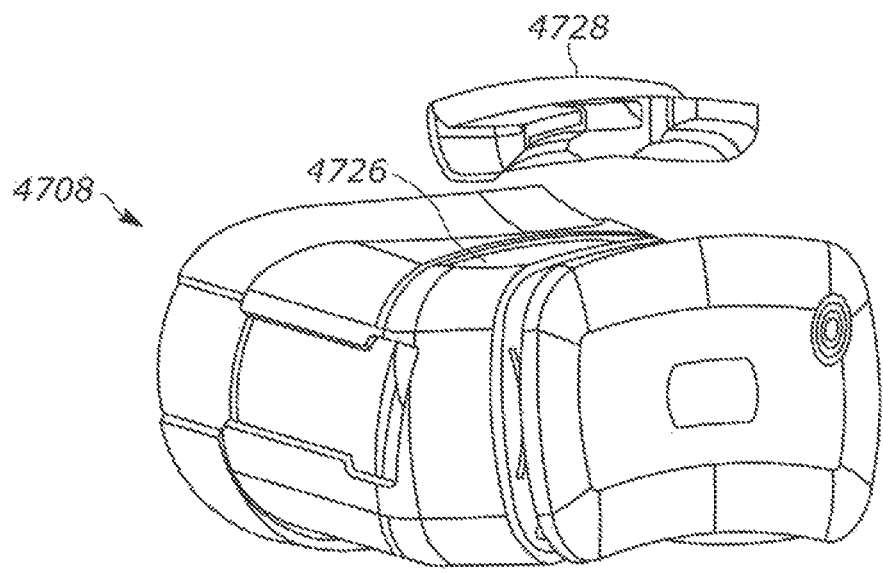
FIG. 47 is yet another view of an exemplary distraction device depicting a removable electronics module.

In the embodiment shown in FIG. 46, a pulse oximetry sensor 4720 is incorporated directly into a notch 4722 of the padding 4724 of the goggles 4704. Thus, when a patient wears the goggles 4704, the pulse oximetry sensor is in direct contact with the patient's forehead. In the embodiment shown in FIG. 47, the goggles 4704 include an electronics module 4728 that is removably insertable into a recess 4726 on the goggles 4704. The electronics module 4728 may be snap-fit or friction-fit into the recess 4726, or otherwise removably attached via various methods known in the art. The electronics module 4728 may include one or more of the sensors described above as well as any other electronics used to transmit signals from the sensors to a computer or other device.

The sensor monitoring provided by the above-mentioned embodiments is particularly important in the context of an unsedated trans-nasal endoscopy or any other procedure involving an unsedated patient disposed in a seated position (especially when unrestrained). In such procedures, the patient is at risk of sudden increased anxiety, such as a panic attack, as well as risk of falling off the chair such as by passing out during the procedure. When a disassociation device 4700 such as the one described above is used in such a procedure, this risk is amplified because the disassociation device 4700 occludes the patient's eyes and parts of the patient's face. Thus, the physician is unable to observe the patient's eyes and face and therefore is unable to detect early warning signs of the patient being in distress. The one or more sensors described above can help detect early signs of such events and warn the physician. For example, if the pulse oximetry sensor 4720 detects decreasing oxygen levels, the patient may be about to pass out and the physician can be warned with warning lights or an alarm sound. Similarly, if a pulse sensor detects an increasing heart rate, the patient may be about to have a panic attack and a similar alarm or warning may sound, including one that is distinguishable from the pulse oximetry sensor 4720 alarm. In one aspect of the present distraction device 4700, the goggles 4704 themselves may automatically act based on input received from the pulse oximetry sensor 4720, pulse sensor, and other sensors described above. For example, if the pulse oximetry sensor 4720 detects decreasing oxygen levels and the patient may be about to pass out or fall asleep, the goggles 4704 may be directed by a computer or other processing unit that receives the data from the sensors to suddenly increase the volume of the audio in the goggles 4704 or flash a warning light from the screen 4706, such as reminding the patient to breathe, etc. Similarly, if the pulse sensor detects increasing heart rate and the patient may be about the have a panic attack, the goggles 4704 may be directed by a computer or other processing unit that receives the data from the sensors to switch to audio or video in the goggles 4704 that is more calming and relaxing or flash a reminder from the screen 4706 to take slow, deep breaths. The other sensors described above may similarly assist in such detection or other useful data collection and analysis by relaying the collected data to a computer or other processing unit to analyze and output a given action.

Figure 48:
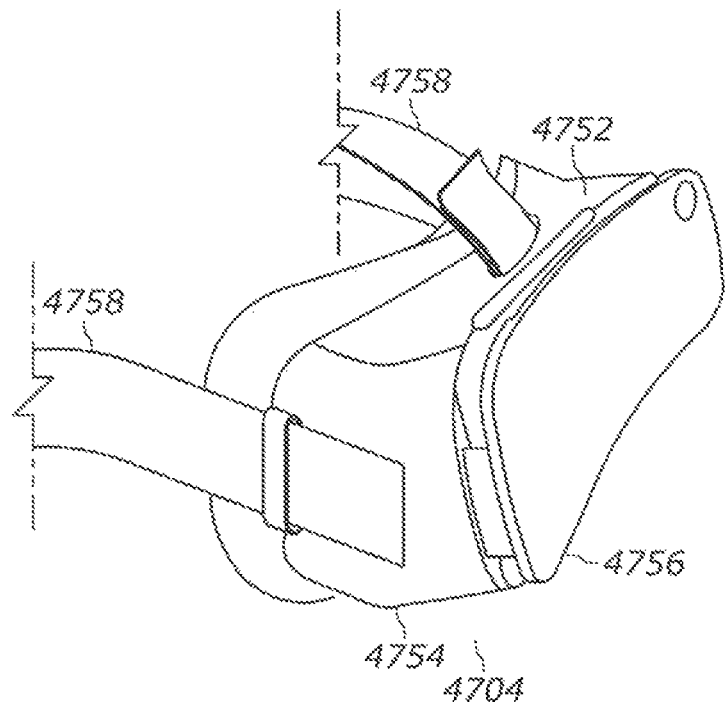
FIG. 48 is a depiction of a phone attachment mechanism for use with goggles.
Figure 49:
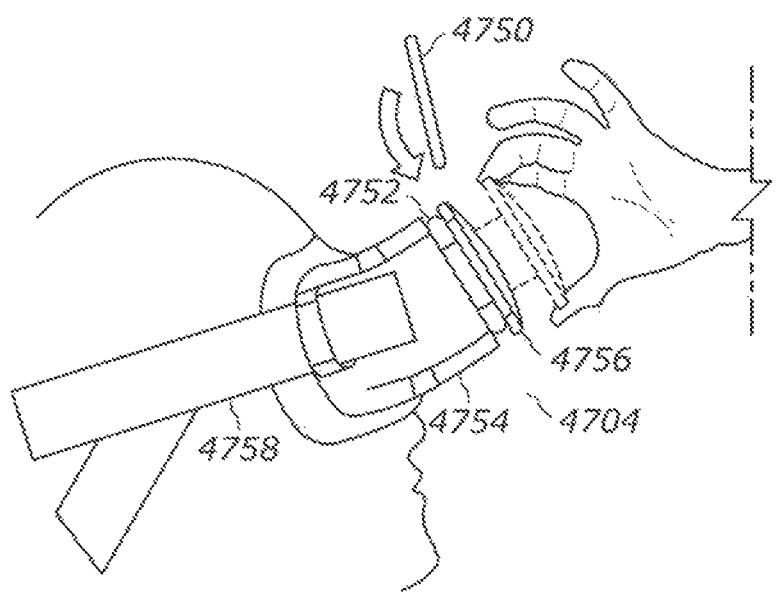
FIG. 49 is another depiction of a phone attachment mechanism for use with goggles.

As described previously, the goggles 4704 of the disassociation device 4700 may use a built-in screen or screens 4706 or may alternatively be designed to receive a phone or other similar device that acts as a screen. FIGS. 48 and 49 show an embodiment of the goggles 4704 to which a phone 4750 or other similar device may be removably connected. As shown in FIG. 49, the phone 4750 may be inserted through a slot 4752 in the goggles 4704. The main body 4754 and door 4756 of the goggles 4704 are separated by the slot 4752. The main body 4754 is attached to the door 4756 via one or more elastic straps 4758. As shown in FIG. 49, the door 4756 can be pulled away from the main body 4754, which causes the elastic straps 4758 to elastically expand or extend. When released, the elastic straps 4758 contract and force the door 4756 back together with the main body 4754 in the rest position. To insert a phone 4750 into the slot 4752, the door 4756 is pulled away from the main body 4754 and the phone 4750 is inserted in the slot 4752. The door 4756 is then released back to its rest position, thereby securing the phone 4750 between the door 4756 and the main body 4754. The elastic straps 4758 may be adjusted, such as by tightening or loosening to further secure or otherwise adjust the position of the phone 4750 in the goggles 4704.

While most of the concepts described above were discussed in the context of the disassociation device 4700 having goggles 4704 with a built-in screen 4706, these concepts are also similarly usable with goggles 4704 that incorporate various sizes of removable phones 4750.

Figure 50:
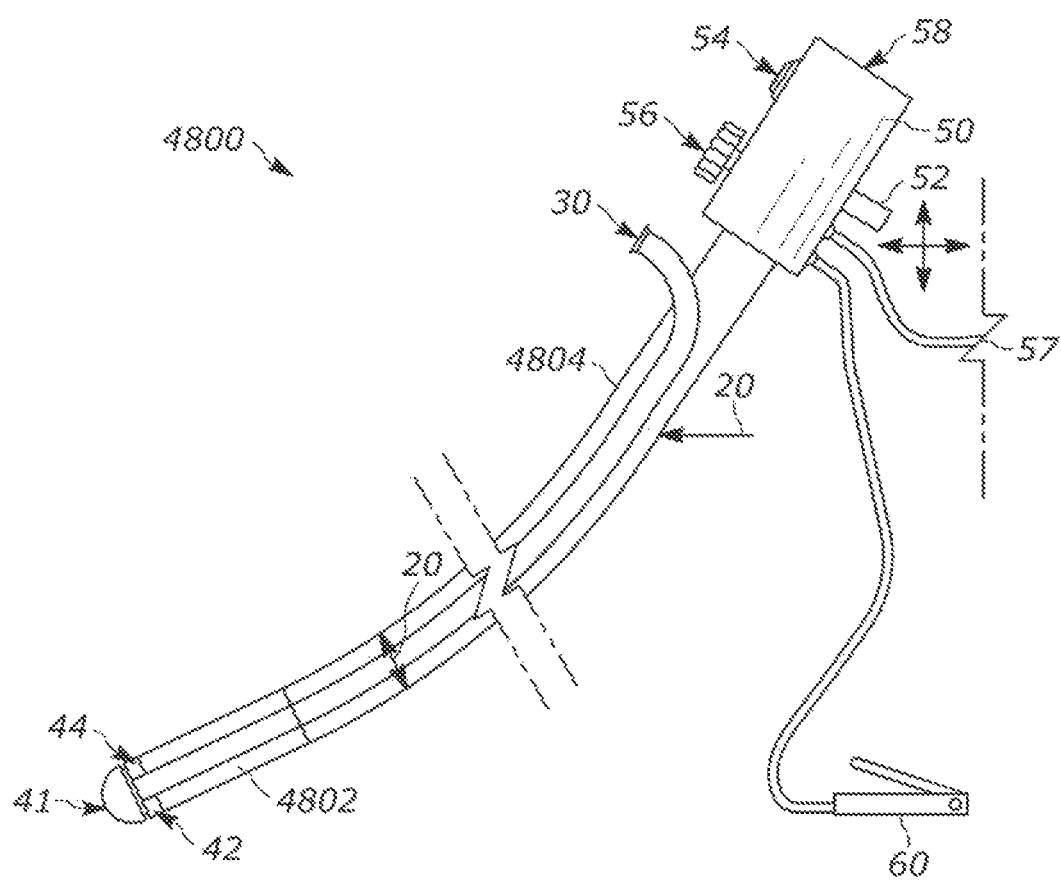
FIG. 50 is a depiction of an endoscope with a detachable distal portion.
Figure 51:
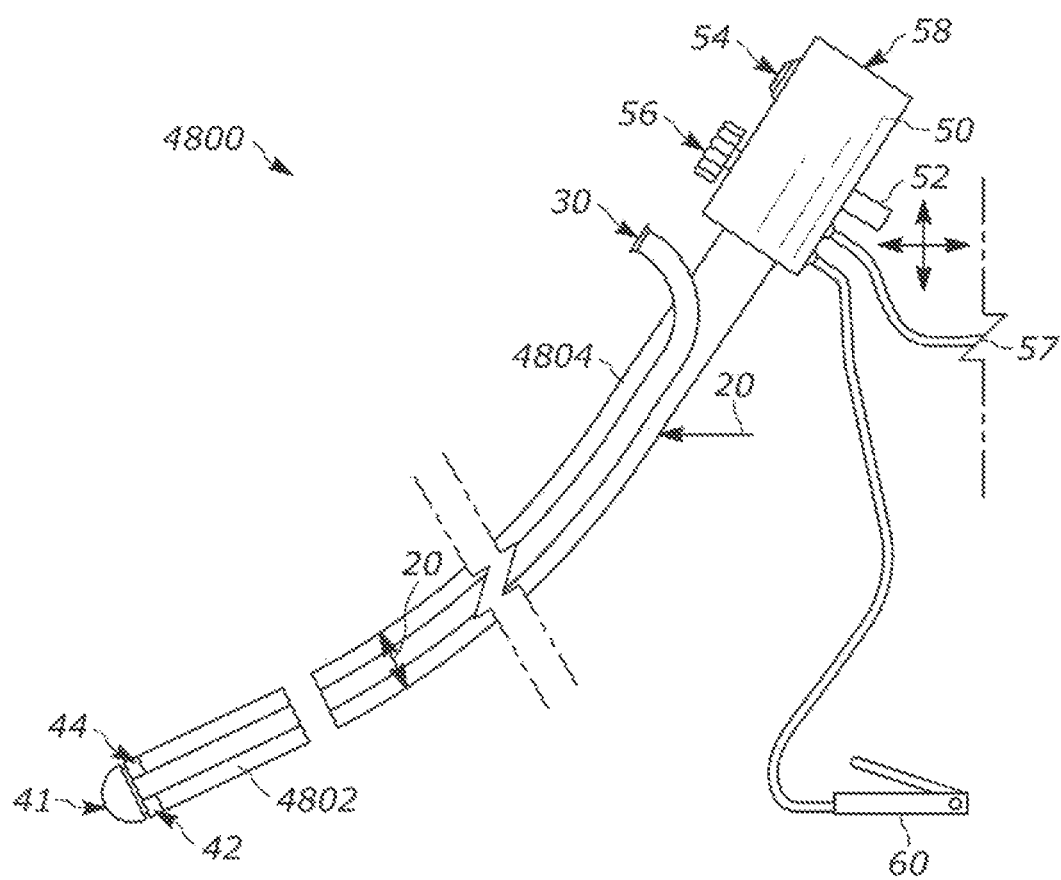
FIG. 51 is another depiction of an endoscope with a detachable distal portion.

FIGS. 50 and 51 depict an endoscope 4800 with an optional detachable distal portion 4802 and retrievable proximal portion 4804. FIG. 48 shows the endoscope 4800 with the distal portion 4802 attached and FIG. 49 shows the endoscope 4800 with the distal portion 4802 detached. The endoscope 4800 may include various features as described with previous embodiments of endoscopes included in this disclosure, including, for example, the embodiment depicted in FIG. 4. Similar structures found on the endoscope 4800 are labeled with the reference numbers used in the FIG. 4 embodiment and a description of these structures can be found in this disclosure with respect to the FIG. 4 embodiment. An operator of the endoscope 4800 may choose to detach the distal portion 4802 during a procedure to continue monitoring the patient after the remainder of the endoscope 4800 is withdrawn from the patient. The distal portion 4802 may either be attached to the patient's body for continuous monitoring, such as by suturing or temporary fixation to a body cavity or other bonding methods known in the art, or detached and allowed to naturally pass through the patient's body while the distal portion 4802 continues to receive sensor inputs and wirelessly relay the data to a computer or other recording device.

The distal portion 4802 of the endoscope 4800 may be detached from the proximal portion 4804 via a variety of methods. For example, the detachment may occur mechanically, via an electromagnet, and other methods. In one non-limiting example, the mechanical detachment can occur via a mechanical engagement between the distal portion 4802 and proximal portion 4804 that is disengaged via a button or lever on the handle of the endoscope 4800.

Uses for the herein-described devices and/or systems may be varied. For example, the devices and/or systems described herein may be used to deliver medications to a target area, remove tissue from a target area, for example to conduct a biopsy, to promote cessation of bleeding/cautery, to remove a foreign body, to collect samples from a target area, in particular bodily fluids, study target areas, in particular the gastrointestinal tract, to evaluate existing and/or potential disease by examining tissues, in particular, pharynx/larynx/esophagus/stomach/small intestine tissues, to diagnose disease or conditions, for example, celiac disease, infection, etc., and/or to manage airways, among others.

The present invention also contemplates the use of the herein-disclosed endoscope for measuring the size of an airway or gastrointestinal tract or other human body cavity, dilation of an airway, gastrointestinal (GI) tract and/or throat, measuring the luminal body cavity pressure exerted by musculature in an airway or gastrointestinal tract, throat and/or other human body cavity, as well as placement of enteral feeding tubes and body devices in an airway and GI tract.

The assemblies, methods and systems described herein can be used to affect tissue which is located on the outside of hollow organs, such as the lung, esophagus, nasal cavity, sinus, colon, vascular vessels and the like, or other solid organs. Various types of activatable elements (e.g., energy emitters) can be utilized to output the energy. The activatable elements can be sufficiently small to facilitate percutaneous delivery to minimize or limit trauma to the patient.

The embodiments disclosed herein can treat the digestive system, urological system, nervous system, vascular system, gynecological, or other systems. The treatment systems and their components disclosed herein can be used as an adjunct during other medical procedures, such as minimally invasive procedures, open procedures, semi-open procedures or other surgical procedures (e.g., lung volume reduction surgery) that provide access to a desired target site. Various surgical procedures on the chest may provide access to lung tissue, the bronchial tree or the like. Access techniques and procedures used to provide access to a target region can be performed by a surgeon and/or a robotic system. Those skilled in the art recognize that there are many different ways that a target region can be accessed.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Any of the endoscopic devices and/or elements thereof described herein may be used in conjunction with a system. Endoscopic systems may include multiple elements as outlined herein.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

It is also to be understood that the following claims are intended to cover all of the generic and specific features of the invention herein described, and all statements of the scope of the invention which, as a matter of language, might be said to fall therebetween.

The present invention will be further illustrated in the following examples which are given for illustrative purposes only and are not intended to limit the invention in any way.

Example 1—Materials and Methods

Subjects ages 8-17 years of age between March 2014 and January 2015 with a defined diagnosis of EoE and who had undergone at least one prior EGD under anesthesia were recruited from the outpatient clinic at Children's Hospital Colorado (CHCO). At the time of the scheduled clinically indicated follow-up appointment, subjects were approached if their primary GI provider felt a follow-up esophagoscopy was needed to evaluate their clinical response to therapy. Subjects were queried if they would be interested in having an unsedated TNE with movie distraction performed instead of a sedated EGD. If so, informed consent was obtained and demographic data collected.

Subjects were instructed to not eat or drink for two hours prior to the TNE. In a standard clinic room, subjects were asked to sit in a chair designed for outpatient laryngoscopic procedures. Two to six sprays of 4% aerosolized lidocaine were applied to the nares to achieve topical anesthesia. Subject distraction was accomplished using either HMZ-T3W 3D movie goggles (Sony Corporation, Tokyo, Japan) or Cinemizer Goggles (Carl Zeiss A G, Oberkochen, Germany) dependent on facial size to facilitate viewing an immersive movie or television program of their choice. Parents remained in the room for the duration of the study procedure. For study design purposes and patient comfort one of two designated pulmonologists (ED, RD) or a single otolaryngologist (JP) performed trans-nasal laryngoscopy using an Olympus BFXP160F 2.8 mm bronchoscope (1.2 mm biopsy channel) in 11/21 subjects and 10/21 subjects using a 4 mm BPMP160F (2 mm biopsy channel) ending with the endoscope in the proximal esophagus. The gastroenterologist (JF) performed esophagoscopy and biopsy collection (three from proximal and three from distal esophagus). Visual confirmation of the adequacy of the biopsy specimens was performed before withdrawing the scope. Data on adverse events, subject symptoms, duration of TNE in five minute intervals up to 15 minutes were collected. After the procedure, families were asked to answer the mGHAA-9 (modified Group Health Association of America) endoscopy satisfaction questionnaire and discharged home.

Subjects were called the evening of the procedure and >72 hours later to evaluate for any adverse events. A minimum of two weeks but not greater than ten weeks after TNE, the subjects and parents were asked to answer an electronic qualitative survey regarding their experience with TNE.

A single pediatric pathologist (KC) evaluated biopsy specimens to assess for size of the sample and inflammatory findings, including eosinophil enumeration. To assure adequate high-power field (hpf) analysis, the total epithelial surface area used to count eosinophils was analyzed using graphical software and analysis (cellSens Standard, 2013, Olympus America, USA). This was accomplished by comparing the subject's available previous esophageal biopsies using a standard 2.8 mm biopsy forceps to the 1.2 or 2 mm biopsy forceps specimens that were collected during TNE.

Charges from TNEs and subjects' previous isolated sedated EGD were collected to compare the cost of the two procedures. Subjects who underwent combined procedures that may have prolonged sedation such as pH probes, pH impedance probes, colonoscopy or flexible sigmoidoscopy at their previous endoscopy were excluded from this calculation (n=12). The University of Colorado Institutional Review Board (COMIRB-13-2721) approved all study procedures.

Data was recorded into a Red-Cap Secure Database. It is reported as a qualitative measure as noted with average, mean and standard deviation (SD). Surface area analysis to assure adequate specimen size was performed using a student's paired, non-parametric, t-test. Charge analysis was performed using unpaired t-test.

Example 2—Evaluation of the Pediatric Nasal Endoscope

Of 22 subjects referred for endoscopy, 22 were contacted and 21 subjects (95.5%) enrolled in this study. One female subject chose not to participate because of "sensory issues." Clinical features of these 21 subjects are shown in Table 1. The average age was 13.04 yrs (+\-2.7 yrs. SD, range from 8-17 years). Subject numbers 1, and 13-21 underwent TNE using the 4 mm endoscope and were aged ranging from 8-16 years. Subject numbers 2-12 underwent TNE using the 2.8 mm endoscope and were aged ranging from 10-17 years. The average number of endoscopies previously performed on the subject cohort was 2.19 (SD+/−1.12). All subjects tolerated TNE with no significant adverse events. Duration of TNE procedures decreased as the endoscopists (JF, ED, JP, RD) became more experienced with TNE. (Table 2). The youngest child was eight years old and was able to tolerate the 4 mm endoscope without difficulty. Symptoms associated with the TNE included gagging and sore throat (Table 3). No adverse event was associated with any emergency department evaluation or unintended evaluation or treatment. One subject had a panic attack prior to the procedure but was still able to complete the TNE without any additional medication. She had a previous history of an anxiety disorder.

Post-procedure assessment revealed a high degree of satisfaction and comfort with the TNE immediately after and at subsequent survey. mGHAA-9 satisfaction instrument average score was 43.19+/−2.6 n=21; maximum 45. A high percentage of subjects reported satisfaction with TNE, child subjects (81%) and parents (90.5%). This is as compared to 81% of combined parent/child subjects satisfied with their previous sedated EGD when asked about it at time of TNE survey. Subjects expressed greater concerns for EGD than TNE on qualitative instrument (61.9% vs. 28.6%, respectively). The majority of children (76.2%) said they would repeat TNE and 100% of parental subjects were willing to have their child undergo the procedure again. More than half of the child subjects (52.4%) preferred TNE, with four subjects not preferring either TNE or sedated EGD, while 85.7% of parental subjects preferred TNE for their child. (Table 4). Reasons for parental preference of TNE included: no anesthesia (61.9%) faster procedure and recovery (52.3%), parental presence during the procedure (28.5%), and lower cost (19%).

Visual TNE findings revealed 11 subjects with normal esophagoscopy, nine with furrowing and one with furrowing and exudates. Visual findings correlated to the appropriate histologic findings in 85.7% of subjects. In those subjects where visual and histological findings did not correlate, two subjects with visual furrowing had normal biopsies, and one with normal appearing mucosa showed histological evidence of eosinophilia <15 eos hpf. (Image 1, Table 5)

Biopsy specimens revealed 12 normal biopsies, four with less than 15 eosinophils per hpf, and five with greater than 15 eosinophils per hpf. (Table 5, Image 1) No significant difference was identified when comparing total epithelial surface area of TNE biopsies to the biopsy surface area of the matched subject's previous EGD. (Table 5) One subject who was initially evaluated at an outside institution did not have his previous biopsies available for analysis. Total epithelial surface area of mucosal biopsies samples from TNE forceps compared to those obtained with standard endoscopic forceps was not statistically different. (0.33 mm$^2$+/−0.09 vs. 0.38 mm$^2$+/−0.14 mm; p=0.308; n=11; TNE 1.2 mm forceps vs. EGD 2.8 mm forceps+/−SD 0.50 mm2+/−0.15 vs. 0.52 mm2+/−0.19; p=0.496, n=9; TNE 2 mm forceps vs. EGD 2.8 mm forceps+/−SD). Although there appears to be a surface area difference between the two 2.8 mm control groups (0.38 mm2 and 0.52 mm2), sub-analysis revealed no significant difference was present using unpaired, non-parametric t-test. (p>0.05)

Of the 21 subjects who underwent TNE, 11 had charge data that was comparable and available for analysis. Charges for TNE were calculated to be 60.1% less than sedated EGD with biopsies, including anesthesia, pathology, facility fees and physician fees.

TABLE 1

Demographics

| Gender (n) | Ethnicity | Age (years) | Average Number of Previous Endoscopies (n) |
|---|---|---|---|
| Male = 13 Female = 9 (1 not enrolled) | Caucasian = 19 (1 not enrolled) Native American = 1 Hispanic = 2 | 13.04 (SD +/−2.7) | 2.26 (SD +/−1.15) |

TABLE 2

Duration of TNE

| Gender (n) | Ethnicity | Age (years) | Average Number of Previous Endoscopies (n) |
|---|---|---|---|
| Male = 13 Female = 9 (1 not enrolled) | Caucasian = 19 (1 not enrolled) Native American = 1 Hispanic = 2 | 13.04 (SD +/−2.7) | 2.26 (SD +/−1.15) |

TABLE 3

Adverse Events

| Self-Reported Symptom | Total Number of Subjects Reportin Symptom |
|---|---|
| Nausea | 4 |
| Choking/Gagging | 12 |
| Sore Throat | 10 |
| Vomiting | 2 |
| Chest Pain | 2 |
| Abdominal Pain | 1 |
| Other | 4 (2 reporting nose discomfort; 2 reporting slightly sore throat) |
| No Significant Symptoms | 7 |

TABLE 4

Satisfaction with the Procedure

| Instrument/Question | Instrument Score |
|---|---|
| mGHAA-9 Score (Max 45 Points) | 43.19 (SD+/−2.6) |
| Qualitative Satisfaction Instrument | Total Subject of 21 total (n) |
| Child: Satisfaction with TNE | 17 (81%) |
| Parent: Satisfaction with TNE | 19 (90.5%) |
| Parent/Child Satisfied with Sedated EGD | 17 (81%) |
| Parent/Child Concerned with Sedated EGD | 13 (61.9%) |
| Child: Willing to Repeat TNE | 16 (76.2%) |
| Parent: Willing to Repeat TNE | 21 (100%) |
| Child: Prefer to Repeat TNE | 11 (52.4%)-4 prefer neither EGD or TNE |
| Parent: Prefer to Repeat TNE | 18 (85.7%)-1 prefer neither EGD or TNE |
| Parent: Qualitative Advantages of TNE | 13/21-No anesthesia<br>11/21-Faster procedure and recovery<br>6/21-Parental presence in the procedure room<br>4/21-Lower cost |

TABLE 5

TNE Findings

| TNE Findin2s | Total Specimens (n) |
|---|---|
| Visually Normal | 11 |
| Slight Furrowing | 2 |
| Furrowing | 8 (I with exudates) |
| Normal Biopsy Abnormality | 12 |
| Eosinophils > 15 hpf | 5 |
| Eosinophils > 15 hpf | 4 |

| Biopsy Forceps | Sample Size | Average Epitheleal Surface Area (mm$^2$) | P-value |
|---|---|---|---|
| EGD 2.8 mm* biopsy forceps | n = 11 | 0.38 (SD 0.14) | P = 0.308 |
| TNE 1.2 mm biopsy forceps | | 0.33 (SD 0.09) | |
| EGD 2.8 mm* biopsy forceps | n = 9 | 0.52 (SD 0.19) | P = 0.496 |
| TNE 2.0 mm biopsy forceps | | 0.50 (SD 0.15) | |

All publications and patent applications mentioned in this specification are herein incorporated by reference to the same extent as if each individual publication or patent application was specifically and individually indicated to be incorporated by reference.

Having thus described in detail preferred embodiments of the present invention, it is to be understood that the invention defined by the above paragraphs is not to be limited to particular details set forth in the above description, as many apparent variations thereof are possible without departing from the spirit or scope of the present invention.

What is claimed is:

1. A method of conducting an unsedated endoscopy exam on a patient, comprising:
   placing a disassociation device over the patient's eyes to at least partially occlude the vision of the patient, wherein the disassociation device comprises a proximal portion aligned with the patient's natural line of sight and a distal portion disposed at an angle above the patient's natural line of sight to expose a nasal passageway of the patient;
   providing a recess in the disassociation device, wherein the recess is configured to removably receive an electronics module;
   setting the patient in a seated still position with the patient having an elevated line of sight;
   providing a cutout in the disassociation device that permits access to the nasal passageway of the patient when the disassociation device is attached to the patient's head;
   inserting at least a portion of an endoscope through the cutout and into the nasal passageway of the patient while the patient is conscious;
   conducting one or more assessments of the patient using the endoscope while the patient is conscious;
   limiting a risk from the one or more assessments of the patient using the endoscope by providing unimpeded access to the nasal passageway, wherein the limited risk is selected from the group consisting of: the risk of turbinate damage, septum damage, increased risk of nose bleed/epistaxis, adenoid damage, sinus damage, potential of cribriform plate damage and injury to brain, increased pain from scope in wrong direction, and increased damage with early nasal endoscopist due to poor technique;
   wherein the elevated line of sight is between about 5 to about 25 degrees from the natural line of sight of the patient; providing information on the position of the endoscope during a procedure with a distance sensor associated with the disassociation device; and
   integrating the distance sensor into a nosepiece of the dissociation device.

2. The method of claim 1, further comprising providing information on the position of the endoscope during the procedure and interpreting body cavity luminal pressuring and sizing-sensing capabilities of the endoscope.

3. The method of claim 2, wherein the detecting the position of the endoscope comprises measuring marks spaced along the length of the endoscope and detecting the presence of each mark by the distance sensor, and determining the distance between each measuring mark.

4. The method of claim 3, wherein the electronics module comprises one or more of a plurality of sensors which is configured to detect at least one of the patient's heart rate, pulse oximetry, blood pressure, sweat content, gas exhalation levels, body temperature, exhalation sounds, respiratory rate, skin elasticity, ocular pressure, pupil sizes, pupil distances, tympanic membrane compliance, hearing aid function, anatomic sizes of luminal objects, and a luminal pressure of a body cavity.

5. The method of claim 4, wherein the disassociation device comprises goggles, wherein the goggles are attachable to the patient's face to at least partially occlude the vision of the patient, wherein the goggles comprise a screen configured to display videos for viewing by the patient.

6. The method of claim 5, wherein the disassociation device is configured to provide a dissociative experience for the patient and a less stressful experience for a physician conducting the one or more assessments of the patient using the endoscope, wherein the method further comprises at least one interaction between the patient and the physician during the step of conducting one or more assessments of the patient.

7. The method of claim 6, wherein the disassociation device provides visual and audio stimuli to the patient to distract the patient.

8. The method of claim 1, further comprising providing a high level of satisfaction to a child patient to repeat the unsedated endoscopy exam.

9. The method of claim 1, further comprising: providing a limited time duration of the procedure and rapid recovery time.

10. The method of claim 1, further comprising providing no significant adverse events and requiring no needed subsequent treatment after the unsedated endoscopy exam.

11. The method of claim 1, further comprising conducting an evaluation of a mucosal sample and providing an evaluation of endoscopic biopsy and forceps position.

12. The method of claim 1, further comprising increasing an efficiency of the unsedated endoscopy exam.

13. The method of claim 1, further comprising reducing a time away from work and school for the patient when compared to a standard sedated pediatric esophagogastroduodenoscopy (EGD).

14. The method of claim 1, wherein the disassociation device comprises goggles, wherein the goggles comprise a screen configured to provide an immersive and/or interactive experience to the patient.

15. The method of claim 1, further comprising moving the patient's head automatically by moving a visual stimuli on the dissociation device and upon moving the patient's head to an appropriate position, the visual stimuli on the dissociation device re-centers to a patient's adjusted gaze.

* * * * *